(12) United States Patent
Trogler et al.

(10) Patent No.: US 9,134,239 B2
(45) Date of Patent: Sep. 15, 2015

(54) THIN LAYER HIGH EXPLOSIVE FLUORESCENT POLYMER SENSING METHODS, SENSORS AND KITS

(75) Inventors: William C. Trogler, Del Mar, CA (US); H. Paul Martinez, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 397 days.

(21) Appl. No.: 13/426,149

(22) Filed: Mar. 21, 2012

(65) Prior Publication Data

US 2014/0017130 A1 Jan. 16, 2014

Related U.S. Application Data

(60) Provisional application No. 61/454,620, filed on Mar. 21, 2011.

(51) Int. Cl.
*G01N 21/75* (2006.01)
*G01N 21/64* (2006.01)
(Continued)

(52) U.S. Cl.
CPC .............. *G01N 21/643* (2013.01); *B82Y 15/00* (2013.01); *B01J 2219/00576* (2013.01); *B01J 2219/00644* (2013.01); *G01N 21/64* (2013.01); *G01N 21/6428* (2013.01); *G01N 33/533* (2013.01)

(58) Field of Classification Search
CPC .............. B01J 2219/00576; B01J 2219/00641; B01J 2219/00644; G01N 21/64; G01N 21/6428; G01N 21/643; G01N 33/533
USPC ......... 422/400, 401, 420, 421, 422, 423, 424, 422/425, 426, 427, 428, 429, 68.1, 82.05, 422/82.06; 436/164, 169, 170; 435/13, 435/283.1, 287.1, 287.7, 287.8, 287.9, 435/288.7
See application file for complete search history.

(56) References Cited

U.S. PATENT DOCUMENTS 5,162,478 A 11/1992 Barton et al.
5,498,736 A 3/1996 Tamao et al.
(Continued)

FOREIGN PATENT DOCUMENTS

KR 2000 0052860 A 8/2008
WO WO 2005/019136 A2 3/2005
(Continued)

OTHER PUBLICATIONS

Bagwe et al, "Surface Modification of Silica Nanoparticles to Reduce Aggregation and Nonspecific Binding" Langmuir 2006, 22, 4357-4362.*

(Continued)

*Primary Examiner* — Dennis M White
(74) *Attorney, Agent, or Firm* — Greer, Burns & Crain, Ltd.

(57) ABSTRACT

A sensor for high explosives, comprising a thin layer of fluorescent polymer covalently linked to a silica support with an oxide surface. The support preferably is a silica support, and in a preferred embodiment is a silica chromatographic support. In preferred embodiments, the fluorescent polymer is one or a few monolayers. A preferred embodiment sensor for high explosives is fluorescent polymer within or upon a porous nanostructure. In preferred embodiments the nanostructure is a porous silica nanoparticle. Embodiments of the invention provide methods, sensors, sensor kits, and sensor fabrication processes that enable detecting traces of high explosives by fluorescence quenching in combination with a chromatographic separation. A method for forming a sensor for high explosives includes preparing a fluorescent polymer, capping the reactive polymer with a reactive capping group that covalently reacts with hydroxide groups, and reacting the reactive capping group with surface hydroxides of an oxide support.

19 Claims, 13 Drawing Sheets

(51) Int. Cl.
*B82Y 15/00* (2011.01)
*G01N 33/533* (2006.01)

(56) References Cited

U.S. PATENT DOCUMENTS

| | | | |
|---|---|---|---|
| 6,169,193 | B1 | 1/2001 | West et al. |
| 6,376,694 | B1 | 4/2002 | Uchida et al. |
| 6,433,356 | B1 | 8/2002 | Cahen et al. |
| 7,482,168 | B2 | 1/2009 | Sailor et al. |
| 7,927,881 | B2 | 4/2011 | Trogler et al. |
| 8,178,357 | B2 | 5/2012 | Trogler et al. |
| 2002/0150759 | A1* | 10/2002 | Jones et al. .................. 428/403 |
| 2002/0167003 | A1 | 11/2002 | Campbell et al. |
| 2005/0054030 | A1 | 3/2005 | Schnoor et al. |
| 2005/0101026 | A1 | 5/2005 | Sailor et al. |
| 2006/0051872 | A1 | 3/2006 | Sailor et al. |
| 2007/0248839 | A1 | 10/2007 | Towns et al. |
| 2009/0137059 | A1 | 5/2009 | Trogler et al. |
| 2010/0173420 | A1 | 7/2010 | Trogler et al. |
| 2010/0176837 | A1 | 7/2010 | Kummel et al. |
| 2010/0291698 | A1 | 11/2010 | Trogler et al. |
| 2011/0057116 | A1 | 3/2011 | Trogler et al. |

FOREIGN PATENT DOCUMENTS

| | | |
|---|---|---|
| WO | WO 2007/024227 A1 | 3/2007 |
| WO | WO 2009023697 A2 * | 2/2009 |

OTHER PUBLICATIONS

Chujo et al, "A Novel Silane Coupling Agent. 1. Synthesis of Trimethoxysilyl-Terminated Poly(N-acetylethylenimine" Macromolecules 1989,22, 2040-2043.*

Sohn, Hongla, et al., "Detection of TNT and Picric Acid on Surfaces and in Seawater by Using Photoluminescent Polysiloles", *Angew. Chem. Int. Ed.*, 2001, vol. 40: No. 11.

Sohn, Honglae; et al., "Detection of Nitroaromatic Explosives Based on Photoluminescent Polymers Containing Metalloles", *American Chemical Society*, 2003, 3821-3830, vol. 125: No. 13.

Toal, Sarah J., et al., "Polymer Sensors for Nitroaromatic Explosives Detection", *Journal of Materials Chemistry*, 2006, 2871-2883, vol. 16.

Yang, Richard D., et al., "Ultralow drift in organic thin-film transistor chemical senors by pulsed gating", *Journal of Applied Physics*, 2007, vol. 102.

Yang, Richard D., et al.,"Ultrathin organic transistors for chemical sensing", *Applied Physics Letters*, 2007, vol. 90.

Pannemann, Ch., et al., "Nanometer scale organic thin film transistors with Pentacene", *Microelectronic Engineering*, 2003, 845-852.

Benfaremo, Nicholas, et al., "Synthesis and Characterization of Luminescent Polymers of Distyrylbenzenes with Oligo(ethylene glycol) Spacers", *Macromolecules*, 1998, 3595-3599, vol. 31:No. 11.

Albizane, Abderrahman, et al., "Organolithium Route to Poly(arylsilane)s", *Polymer International*, 1991, 93-96, vol. 26.

Bouvet, Marcel, "Phthalocyanine-based field-effect transistor as ozone sensor", *Sensors and Actuators B*, 2001, 63-70, vol. 73.

Chang, Josephine B., et al., "Effect of active layer thickness on bias street effect in pentacene thin-film transistors", *Applied Physics Letters*, 2006, vol. 88.

Ruiz, Ricardo, et al., "Thickness Dependence of Mobility in Pentacene Thin-Film Transistors", *Advanced Materials*, 2005, 1795-1798, vol. 17.

Dinelli, Franco, et al., "Spatially Correlated Charge Transport in Organic Thin Film Transistors", *Physical Review Letters*, 2004, vol. 92: No. 11.

Yang, Richard D., et al., "Chemical identification using an impedance sensor based on dispersive charge transport", *Applied Physics Letters*, 2006, vol. 88.

Miller, Karla A., et al., "Electrode Independent Chemoresistive Response for Cobalt Phthalocyanine in the Space Charge Limited Conductivity Regime", *J. Phys. Chem B*, 2006, 361-366, vol. 110: No. 1.

Schmechel, Roland, et al., "Electronic traps in organic transport layers", *phys. stat. sol.*, 2004, 1215-1235, vol. 201: No. 6.

Horowitz, Gilles, "Organic thin film transistors: From theory to real devices", *J. Mater. Res.*, 2004, vol. 19: No. 7.

Bouvet, Marcel, "Phthalocyanine-based field-effect transistors as gas sensors", *Anal Bioanal Chem.*, 2006, 366-373, vol. 384.

Chang, Josephine B., et al., Printable Polythiophene gas sensor array for low-cost electronic nose, *Journal of Applied Physics*, 2006, vol. 100.

Zhu, Zheng-Tao, et al., "Humidity sensors based on pentacene thin-film transistors", *Applied Physics Letters*, Dec. 9, 2002, vol. 81: No. 24.

Someya, Takao, et al., "Vapor sensing with $\alpha,\omega$-dihexylquarterthiophene field-effect transistors: The rold of grain boundaries", *Applied Physics Letters*, Oct. 14, 2002, vol. 81: No. 16.

Wang, Liang, et al., "Nanoscale chemical sensor based on organic thin-film transistors," *Applied Physics Letter*, Dec. 27, 2004, vol. 85: No. 26.

Salleo, A., et al., "Light-induced bias stress reversal in polyfluorene thin-film transistors," *Journal of Applied Phyisics*, Jul. 1, 2003, vol. 94: vol. 1.

Yang, Shane-Jye, et al., "Fluorescent Porous Polymer Films as TNT Chemosensors: Electronis and Structural Effects", *American Chemical Society*, 1998, vol. 120: No. 46.

Zhou, R., et al., "Phthalocyanines as Sensitive Materials for Chemical Sensors," *Applied Organometallic Chemistry*, 1996, 557-577, vol. 10.

Gould, G.D., "Structure and electrical conduction properperties of phthalocyanine thin films," *Coordination Chemistry Reviews*, 1996, 237-274, vol. 156.

Yang, Jye-Shane, et al., "Porous Shape Persistent Fluorescent Polymer Films: An Approach to TNT Sensory Materials," *J. American Chemical Society*, 1998, vol. 120: No. 21.

Carre, M.-C., et al., "Fluorimetric nitrit analysis using 2,3-diaminonaphthalene: an improvement of the method", *Analysis*, 1999, 835-838, vol. 27.

Guillaud, G., et al., "Metallophthalocyanines Gas sensors, resistors and field effect transistors", *Coordination Chemistry Reviews*, 1998, 1433-1484.

Wang, Ergang, et al., "Poly(3,6-silafluorene-co-2,7-fluorene)-based high-efficiency and color-pure blue light-emitting polymers with extremely narrow band-width and high spectral stability", *Journal of Materials Chemistry*, 2006, 4133-4140, vol. 16.

Kim, Ji Ho., et al., "Oxidative Couling Polymerization of Diethynylsilane Derivatives and 1,2,-Diethynyl-1,1,2,2-tetramethyldisilane", *Bull Korean Chem. Soc.*, 2006, vol. 27: No. 6.

Toal, Sarah J., et al., "Luminescent oligo(tetraphenyl)silole nanoparticles as chemical sensors for aqueous TNT", *Royal Society of Chemistry*, 2005, 5465-5467.

Toal, Sarah J., et al., "Syntheses of Oligometalloles by Catalytic Dehydrocoupling" *Organmetallics*, 2005, 3081-3087, vol. 24.

Ohshita, J., et al., "Polymers with alternating organosilicon and $\pi$-conjugated units", *Acta. Polym.*, 1998, 379-403, vol. 49.

Chauhan, Bhanu P.S., et al., "New Vistas in Dehydrocoupling Polymerization of Hydrosilanes: Platinum Complex-Catalyzed Dehydrocoupling of Cyclic and Acyclic Secondary Silanes", *Chemistry Letters*, 1997.

Pang, Y., et al., "Catalytic Syntesis of Silyene-Vinylene Preceramic Polymers from Ethynylsilanes", *Macromolecules*, 1993, 5671-5675, vol. 26.

Luneva, L.K., et al., "Synthesis of Organosilicon and Organogermanium Polymers Containing Diacetylenic Groupings in the the Chain", *Russian Chemical Bulletin*, 1968, 160-163, vol. 17.

Korshak, V.V., et al., "Heteroorganic Polymers", *Russian Chemical Bulletin*, 1962, 2153-2155, vol. 11.

Corriu, Robert J.P., et al., "Sythesis of Poly (alkynylsilanes) having Various Aromatic Groups in the Backbone", *Journal of Polymer Science: Part C: Polymer Letters*, 1990, 431-437, vol. 28.

Sohn, Honglae, et al., "Detection of Nitroacromatic Explosives Based on Photoluminescent Polymers Containing Metalloles", *JACS*, 2003, 3821-3830, vol. 125.

(56) References Cited

OTHER PUBLICATIONS

"Expray Explosive Detection Kit", *Plexus Scientific Cooperation*, http://expray.plexsci.com/site/index/products/kits/explosionskits/ex.html, Nov. 8, 2010.

Andrew, Trisha L., et al., "A Fluorescence Turn-On Mechanism to Detect High Explosives RDX and PETN", *J. AM. Chem. Soc.*, 2007, 7254-7255, 129.

Toal, Sarah Josepha, Photoluminescent Metalloles for Chemical Sensing of Nitroaromatic Explosives and Chromium(VI), *UMI Microform*, 2005.

Sawicki, T.W., et al., "Direct Fluorometric Scanning of thin-layer Chromatograms and its application to air pollutions studies", *Journal of Chromatography*, 1965, 348-353, vol. 20.

Gholamian, Forouzan, et al., Determination of RDX and Keto-RDX in High-Explosive Mixtures by High Performance Thin-Layer Chromatorgraphy, *Journal of Planar Chromatography*, 2001, vol. 14.

Livermore, Lawrence, "Forensic Science Center Maximizes the Tiniest Clue", *Forensic Science Center*, 2002.

Sanchez, Jason C., et al., "Lewis acid-base interactions enhance explosives sensing in silacycle polymers", *Anal Bioanal Chem.*, 2009, 387-392, vol. 395.

Sanchez, Jason C., et al., "Catalytic Hydrosilylation Routes to Divinylbenzene Bridged Silole and Silafluorene Polymers. Applications to Surface Imaging of Explosive Particulates", *Macromolecules*, 2008, 1237-1245, vol. 41.

Toal, Sarah J., "Luminescent oligo(tetraphenyl)silole nanoparticles as chemical sensors for aqueous TNT", *The Royal Society of Chemistry*, 2005, 5465-5467.

Yinon, Jehuda, "Field detection and monitoring of explosives", *Trends in Analytical Chemistry*, 2002, vol. 21: No. 4.

Sanchez, Jason C., et al., "Efficient blue-emitting silafluorene-fluorene-conjugated copolymers: selective turn-off/turn-on detection of explosives", *The Royal Society of Chemistry*, 2008, 3143-3156, vol. 18.

Yang, Jian, et al., "Hollow silica nanspheres containing a silafluorene-fluorene conjugated polymer for aqueous TNT and RDX detection", *The Royal Society of Chemistry*, 2010, 6804-6806, vol. 46.

Reynolds, J.G., et al., "On-site Analysis of Explosives in Various Matrices", *Lawrence Livermore National Laboratory*, Jan. 30, 2006.

Toal, Sarah J., et al., "Visual Detection of Trace Nitroaromatic Explosive Residue Using Photoluminescent Metallole-Containing Polymers", *Journal of Forensic Sciences*, 2007, vol. 52, No. 1.

Sanchez, Jason C., et al., "Synthesis, Luminescence Properties and Explosives with 1,1-Tetraphenylsilole- and 1,1-Silafluorene-vinylene Polymers", *Chem. Mater.*, 2007, 19, 6459-6470.

\* cited by examiner

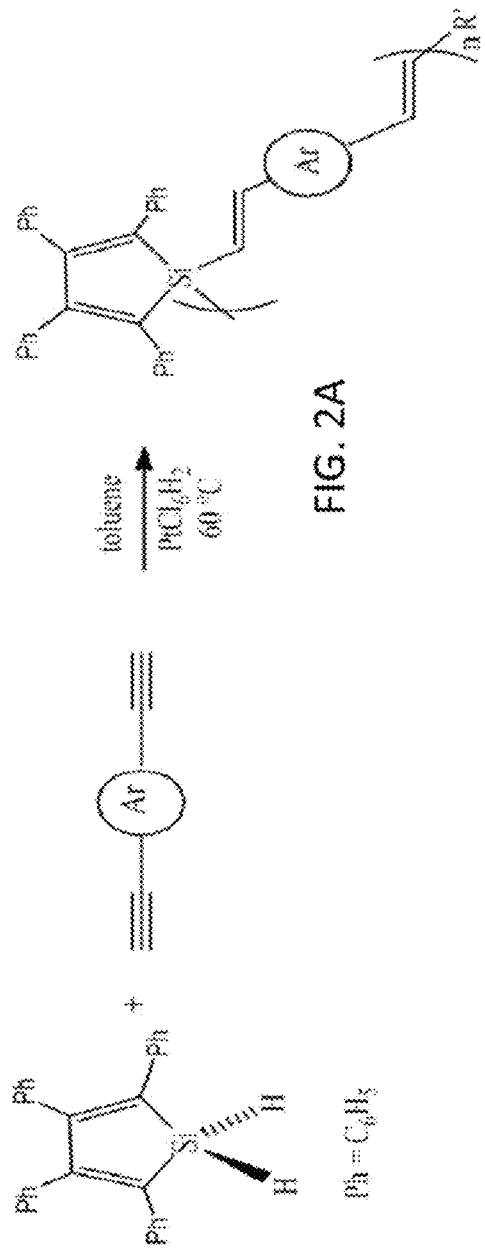
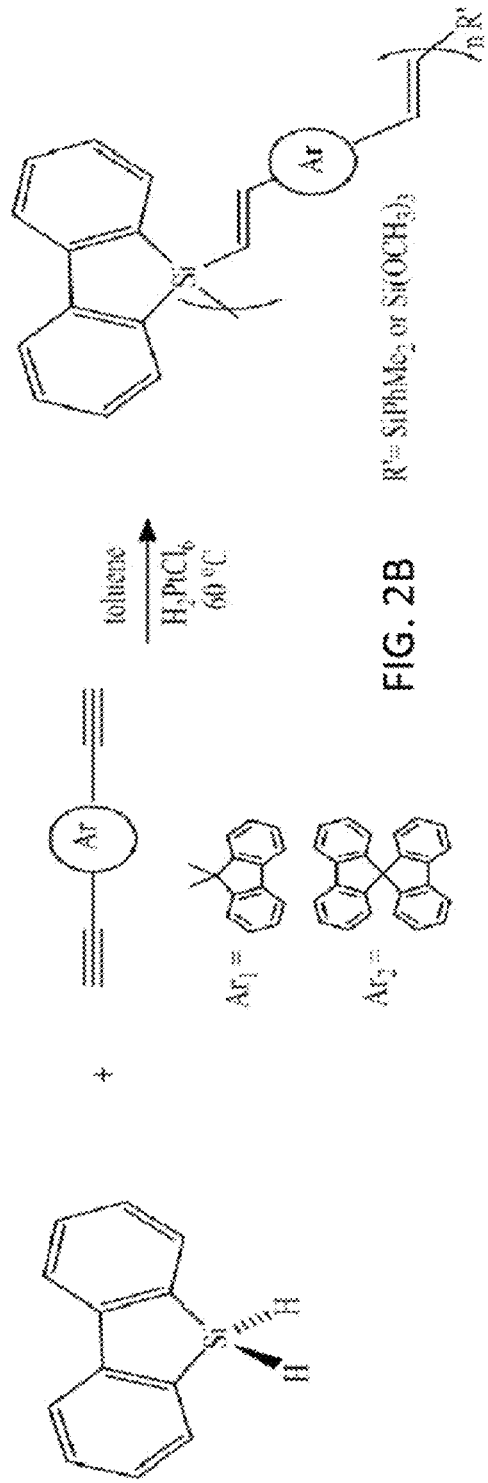
FIG. 2A
FIG. 2B

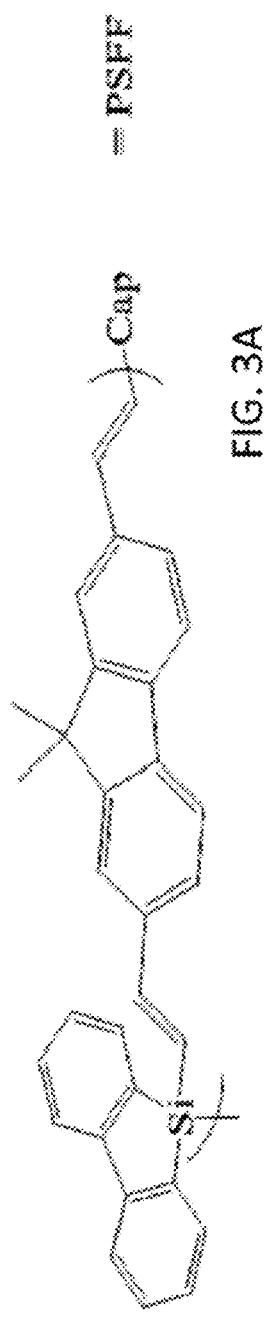
FIG. 3A = PSFF
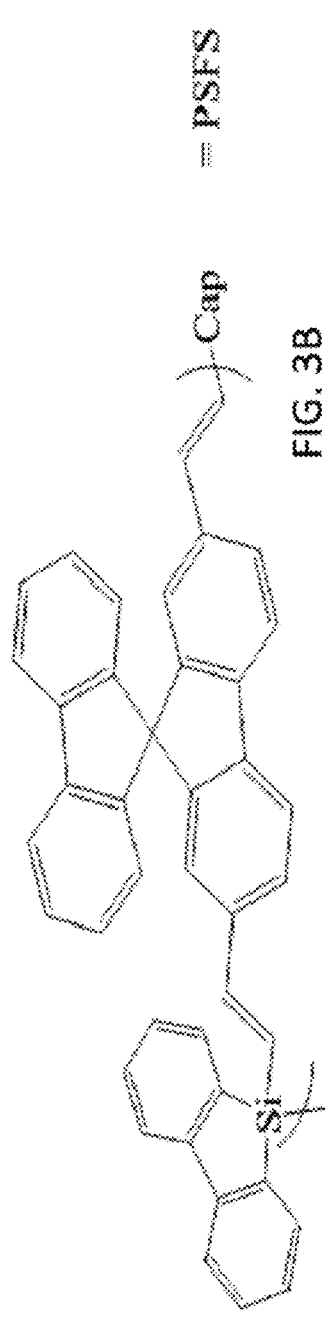
FIG. 3B = PSFS
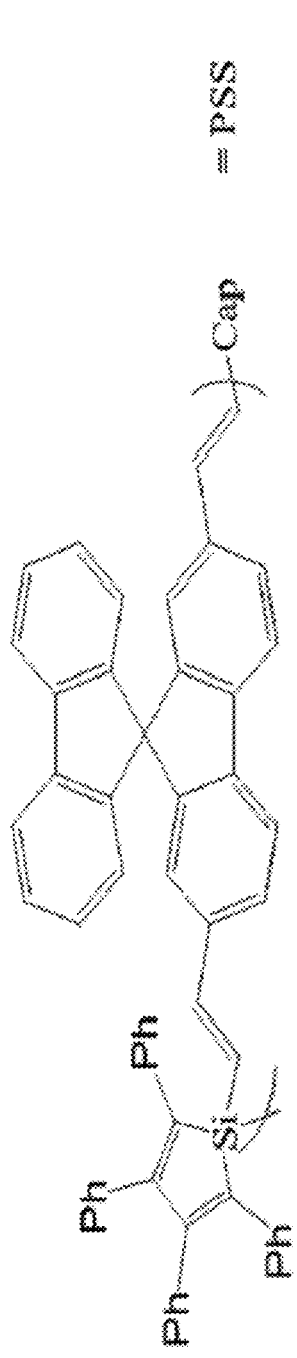
FIG. 3C = PSS
Cap = SiMe$_2$Ph or Si(OCH$_3$)$_3$

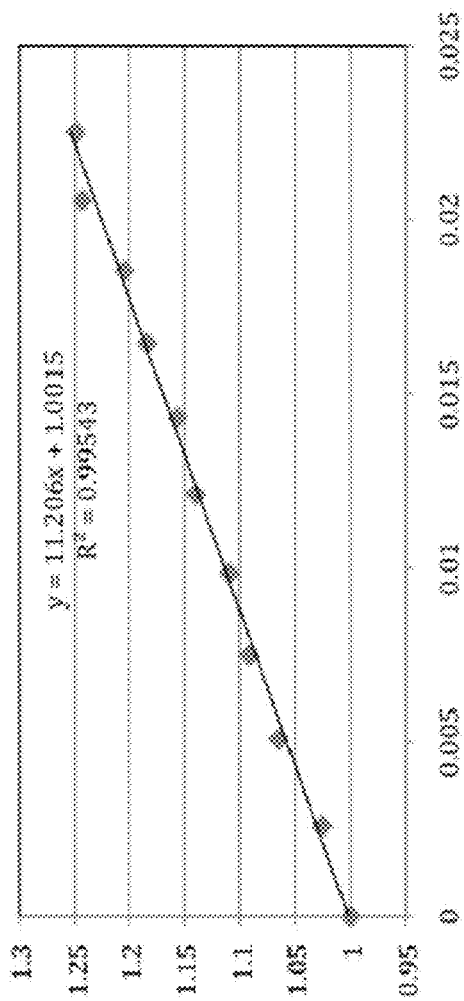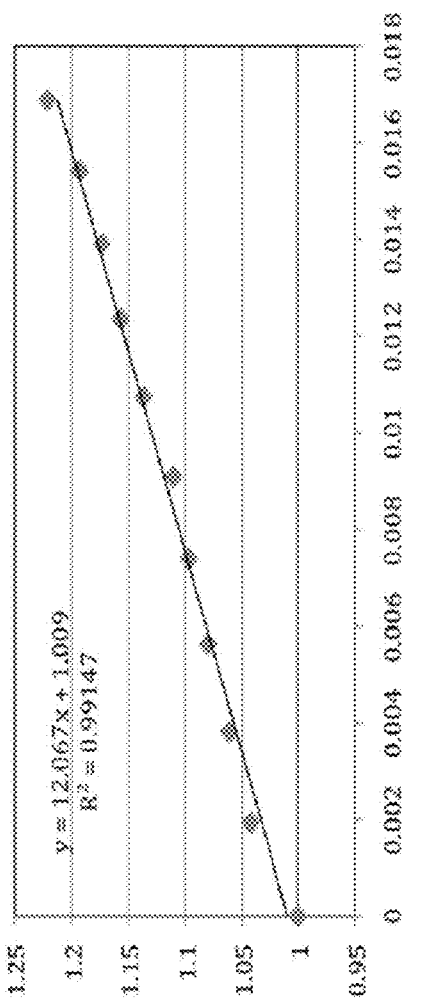
FIG. 6A
FIG. 6B

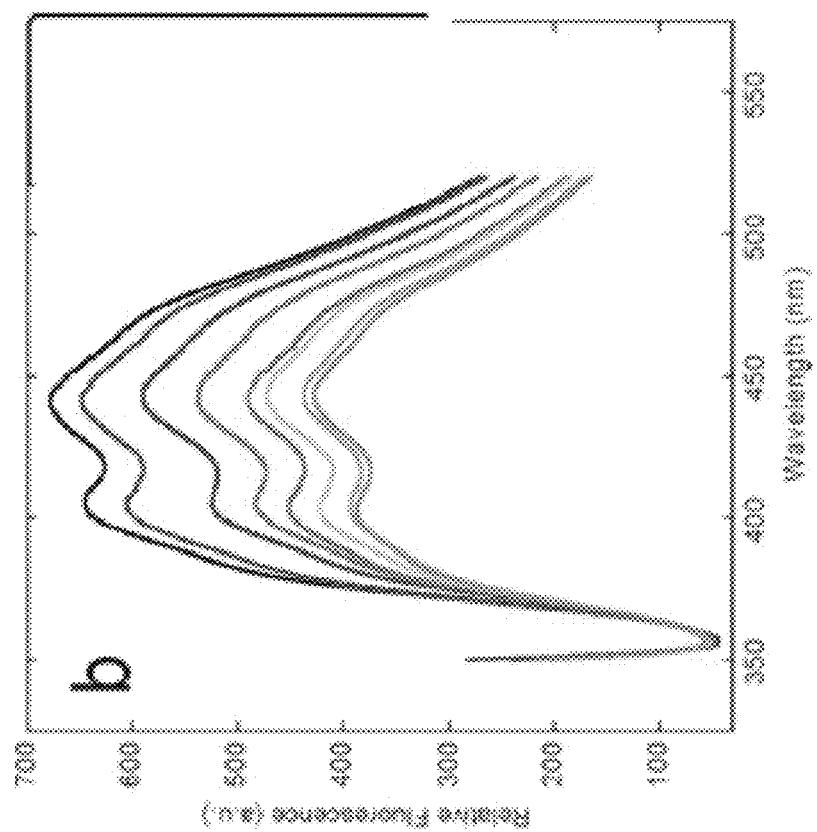
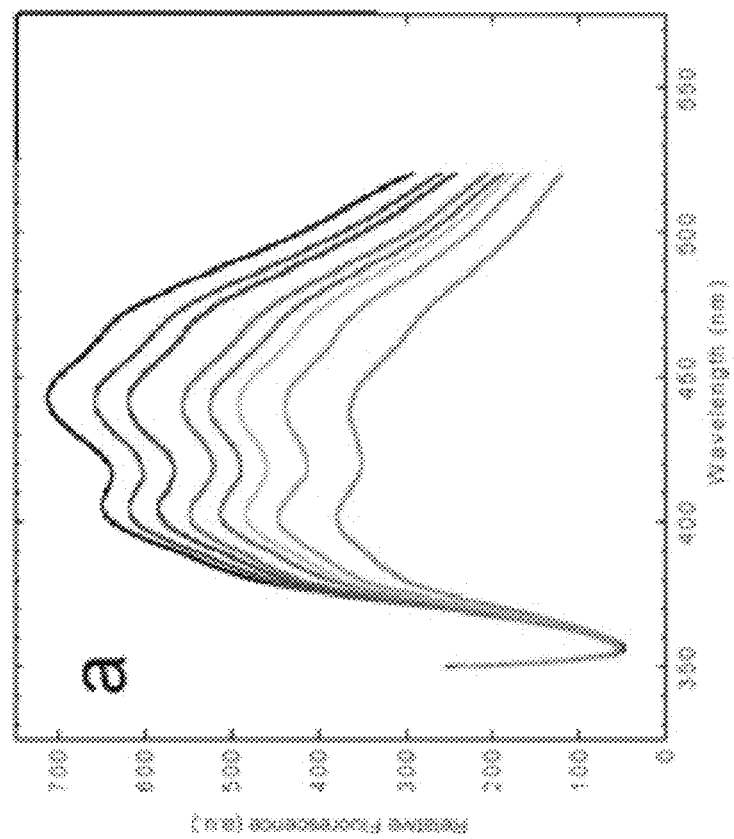
FIG. 8B
FIG. 8A

THIN LAYER HIGH EXPLOSIVE FLUORESCENT POLYMER SENSING METHODS, SENSORS AND KITS

PRIORITY CLAIM AND REFERENCE TO RELATED APPLICATION

The application claims priority under 35 U.S.C. §119 from prior provisional application Ser. No. 61/454,620, which was filed Mar. 21, 2011 and entitled Thin Layer High Explosive Fluorescence and Chromatographic Sensing Methods, Sensors and Kits.

FIELD

A field of the invention is high explosive sensing methods, sensors and kits. Example applications of the invention include the detection of high explosives in trace amounts.

BACKGROUND

Explosive detection in many environments, such as military facilities, minefields, remediation sites, as well as mass transit areas has unfortunately become a necessity. Chemical sensors have shown a high aptitude for the detection of trace levels of explosives. For that reason, there remains a demand for inexpensive and reliable explosive sensors to be used in a field setting for identifying specific explosives.

The majority of chemical sensors are based upon small synthetic molecules that produce a measurable signal upon interaction with a specific analyte. Chemical sensors are cost effective and have been shown to succeed where other techniques fail to effectively detect explosives. For example, modern land mines are encased in plastic and can be easily missed by metal detectors. Trained explosive sniffing dogs are effective, but require extensive, expensive training and can be difficult to maintain. Other detection methods, such as gas chromatography coupled with a mass spectrometer, surface-enhanced Raman, nuclear quadrupole resonance, energy-dispersive X-ray diffraction, neutron activation analysis and electron capture detection are highly selective. These methods are expensive and from not easily transported systems that are difficult to deploy and utilize in a field setting.

There are many commercially available chemical sensors that function very well under many circumstances, however all have limitations that render them ineffective under some conditions. The detection of TNT (2,4,6-trinitrotoluene) and picric acid in groundwater or seawater can be critical for the detection of buried, undetonated ordinances or for locating underwater mines. This can be problematic for chemical sensors because most chemical sensing detection methods are optimized for air samples. Interference problems are encountered in complex aqueous media. Standard chemical sensors can therefore be inefficient in environmental applications for characterizing soil and groundwater contaminated with toxic explosives at military bases and munitions production and distribution facilities.

Conventional chemical sensors, such as highly π-conjugated, porous organic polymers, can be used to detect vapors of electron deficient chemicals, but require many steps to synthesize, are not always selective to explosives and cannot be considered a cost effective disposable sensor. The problem of vapor detection is further hampered when the vapor pressure of explosives is considered.

Organic and silicon metallole hybrid polymers developed by the present inventors and colleagues have shown the ability to detect explosives by way of fluorescent quenching even in complex media. For example, Sailor et al., U.S. Pat. No. 7,482,168 entitled Photoluminescent Polymetalloles as Chemical Sensors, discloses methods for detecting electron deficient nitroaromatic molecules in air, water or other surfaces that employ a thin film of photoluminescent copolymers, which are stable in air, water, acids, common organic solvents, and even seawater containing bioorganisms. The polymers contain metalloid-metalloid backbones such as Si—Si, Si—Ge, or Ge—Ge. The detection method involves measurement of the quenching of photoluminescence of the polysilole by the analyte. Trogler et al., U.S. Pat. No. 7,927,881 entitled Inorganic Polymers and Use of Inorganic Polymers for Detecting Nitroaromatic Compounds, discloses sensing methods and sensors including an inorganic-organic metallole-containing polymer or copolymer with a backbone including carbon atoms bonded to metalloid atoms. Additional sensors and sensing methods are disclosed in Sohn et al., "Detection of Nitroaromatic Explosives Based on Photoluminescent Polymers Containing Metalloles," J. Am. Chem. Soc., 2003, 125 (13) pp. 3821-30 (2003); Sohn et al., "Detection of TNT and Picric Acid on Surfaces and in Seawater by Using Photoluminescent Polysiloles," Angew. Chem. Int., vol. 40, No. 11, pp. 2104-2105 (2001).

Most high explosives are organic nitrates, nitramines, and nitro based compounds. High explosives are considered to be organic and oxidizing, a relatively rare combination that makes them tractable for molecular recognition-binding event involving hydrophobic interactions, followed by electron transfer quenching of a fluorophore. The Lewis acid nature of the Si atom also permits coordination of oxygen lone pairs from the analyte, providing an efficient electron transfer pathway. For this reason, fluorescent silole hybrid polymers have had favorable success in their use as high explosive sensors.

Fluorescence quenching polymers selective for nitroaromatics have been demonstrated to allow for separation and identification of nitroaromatic explosives, such as TNT, DNT, tetryl, and TNB through a combination of fluorescence quenching and chromatographic retention time. For other high explosives (e.g., PETN, RDX, HMX) a fluorescent polymer capable of detecting these explosives is used if the sample is negative for nitroaromatics. Through a combination of fluorescence quenching and by the characteristic chromatographic retention time, the high explosive can be identified. In typical prior sensing methods, this class of organosilicon polymers have been dissolved and sprayed onto solid supports as aerosols to provide a sensor.

Decades ago, Sawicki, et al. pioneered the use of TLC separation and fluorescence quenching in the identification of over 20 different polyaromatic hydrocarbon (PAH) compounds present in environmental combustion aerosols. E. to Sawicki et al., "Direct Fluorometric Scanning of Thin-layer Chromatograms and its Application to Air Pollution Studies," Journal of Chromatography Vol. 20, lines 348-353. These methods rely on quenching the fluorescence of the PAH itself with organic nitro compounds, and detection limits as low as 10 ng were achieved. Colorimetric reagents have been used previously to further identify PAH compounds, including TNT, with the use of TLC and paper chromatography, but such methods are limited to detection limits of microgram quantities. Thin layer chromatography in conjunction with optical absorption measurements has been used to separate explosives and identify compositions of explosive mixtures, but did not provide for trace detection. See, e.g., "Determination of RDX and ket9-RDX in High-explosive Mixtures by High-performance Thin-Layer Chromatography," J. Planar Chrmmatog, 14 (2001) 296-299.

SUMMARY OF THE INVENTION

An embodiment of the invention is a sensor for high explosives, comprising a thin layer of fluorescent polymer covalently linked to a silica support with an oxide surface. The support preferably is a silica support, and in a preferred embodiment is a silica chromatographic support. In preferred embodiments, the fluorescent polymer is one or a few monolayers. Another preferred embodiment sensor for high explosives is a fluorescent polymer within or upon a porous nanostructure. In preferred embodiments, the nanostructure is a porous silica nanoparticle. Embodiments of the invention provide methods, sensors, sensor kits, and sensor fabrication processes that enable detecting traces of high explosives by fluorescence quenching in combination with a chromatographic separation. A method for forming a sensor for high explosives includes preparing a fluorescent polymer, capping the reactive polymer with a reactive capping group that covalently reacts with hydroxide groups, and reacting the reactive capping group with surface hydroxides of a support.

BRIEF DESCRIPTION OF THE DRAWINGS

FIGS. 2A-2B show a synthetic scheme used to create polymers in experiments via dihydrosilole and dihydrosila-fluoroene polymerization;

FIGS. 3A-3C are structural representations of preferred embodiment organosilicon polymer with capping moieties that were prepared in experiments to demonstrate a sensor and sensing method of the invention;

FIGS. 6A-6D show the Stern-volmer quenching plots with the explosives: RDX, HMX, CL-20, and PETN in cyclohexanone and acetone (PETN) solvents, respectively;

FIGS. 8A-8B respectively show quenching with incremental concentrations of TNT and RDX in a solution of PSFF coated silicon nanoparticles of the invention.

DETAILED DESCRIPTION OF THE PREFERRED EMBODIMENTS

Figure 1A:
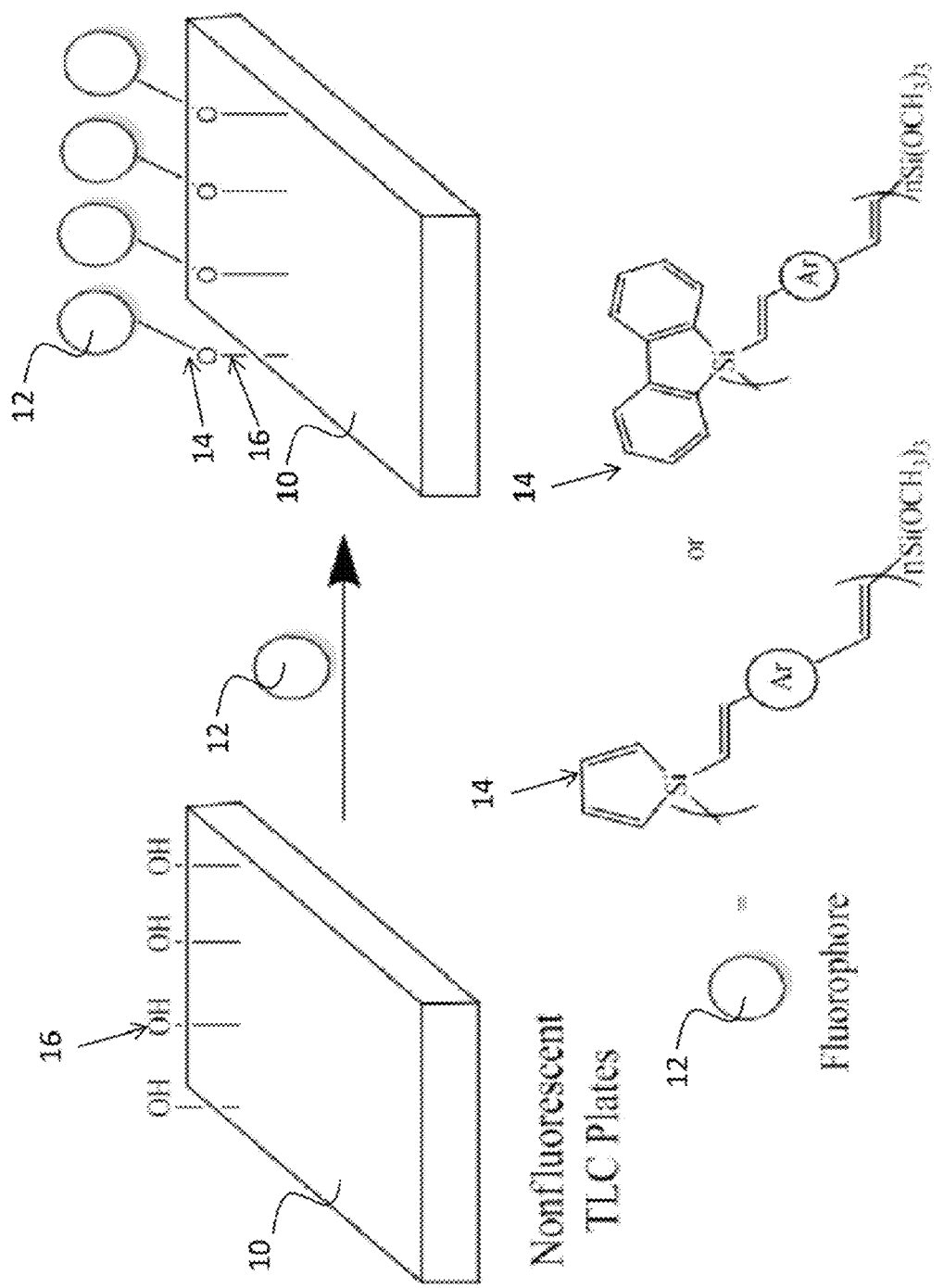
FIG. 1A is a schematic representation of a process for forming a sensor and a sensor with a chromatographic silica support according to a preferred embodiment of the invention.

Embodiments of the invention provide methods, sensors, sensor kits, and sensor fabrication processes that enable detecting traces of high explosives by fluorescence quenching in combination with a chromatographic separation. A preferred embodiment sensor of the invention has fluorescent, silicon based polymers that are covalently linked to a silica thin layer chromatographic plate and nanoparticle supports. A thin, covalently bonded layer of the polymer allows for a more efficient interaction with an analyte, thus yielding enhanced detection sensitivity. The covalent attachment is via a surface oxide. The attachment of the sensing polymers onto a chromatographic support in preferred sensors allows for the separation of a mixture, as well as the identification of multiple explosives through the use of multiple sensing polymers. The covalent attachment of the sensing polymer onto a silica nanoparticle in preferred sensors permits the detection of high explosives in an aqueous media. In other embodiments, the sensing polymer is adsorbed by the nanoparticle. Preferred sensing polymers include copolymers of silafluorene, silole, spirofluorene and fluorene and their derivatives. In addition to silica based supports, including silica nanoparticles, other supports can be used. Oxide coated supports, including nanoparticles and nanostructures, permit covalent attachment of the sensing polymers. In addition, porous nanostructures permit adsorption of the sensing polymers.

In embodiments of the invention, fluorescence quenching polymers are selective for nitroaromatics and allow a separation and identification of nitroaromatic explosives, such as TNT, DNT, tetryl, and TNB through a combination of fluorescence quenching and chromatographic retention time. Other high explosives (PETN, RDX, HMX) can be detected with a fluorescent polymer capable of detecting these explosives if the sample is negative for nitroaromatics and through a combination of fluorescence quenching and by the characteristic retention time. Previously, this of class polymers have been dissolved and sprayed onto solid supports as aerosols. With preferred embodiments of the present invention, the fluorescence quenching polymers are covalently attached, for example to a solid silica support, thin layer chromatographic plates (TLC) and hollow silica nanoparticles.

A preferred embodiment sensor is provided that essentially consists of one or a few monolayers of polymer covalently attached to the surface of a support. The covalently attached one or a few monolayers is believed to minimize self-quenching from polymer-polymer interaction, thereby allowing for more complete analyte interaction, and to therefore provide even lower detection limits than prior sensors using the same polymers that are merely dissolved and sprayed onto solid supports. Furthermore, since the solid support being utilized is preferably a chromatographic support, mixtures of explosives can be separated into components.

Preferred embodiments use fluorescent organosilicon polymers. Additional preferred embodiment sensors and sensing methods are based upon and include copolymers of silafluorene, silole, spirofluorene and fluorene and derivatives that are adsorbed or covalently attached to silica nanoparticles and silica gel surfaces. Other element oxide nanostructures and surfaces, such as aluminum oxide, are expected to behave similarly as the mechanism for covalent attachment, in embodiments of the invention that utilize covalent attachment, relates to the ambient oxide surface. In addition, porous nanostructures permit adsorption of the sensing polymers. In the case of a nanoparticle or other nanostructure, a surface of the shell can be modified into a pseudo organic environment, which can then interact and solubilize the insoluble explosive molecules. Excellent detection in aqueous solutions have been demonstrated with silica nanoparticles.

Sensors and methods of the invention can detect traces of high explosives by fluorescence quenching in combination with a chromatographic separation. The use of a fluorescence quenching polymer selective for nitroaromatics allows a separation and identification of nitroaromatic explosives, such as TNT, DNT, tetryl, and TNB through a combination of fluorescence quenching and chromatographic retention time. For other high explosives (PETN, RDX, HMX) a fluorescent polymer capable of detecting these explosives is used if the sample is negative for nitroaromatics and through a combination of fluorescence quenching and by the characteristic retention time, the high explosive can be identified.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

FIG. 1A illustrates a process to form a sensor of the invention in which fluorescent polymers are covalently linked to a silica gel thin layer chromatography (TLC) support 10. The support is non-fluorescent. Fluorophores 12 are attached covalently to the support 10 via end capping moieties 14. The covalent attachment of fluorescent polymers can be achieved via a condensation reaction of the surface hydroxides 16 of the silica with a trimethoxysilyl cap/end group 14 of the polymers. While a silica gel thin layer chromatography (TLC) support 10 is a preferred embodiment, silica nanoparticles are another preferred support, as the nanoparticles are also hydroxide terminated. Suitable end capping moieties includes $Sj(OC_2H_5)_3$ and $Si(OCH_3)_3$. Capping can achieved by hydrosilation of the terminal alkyne group of a polymer with trimethoxysilane. This provides a reactive end group for covalent attachment to a silica surface. In preferred embodiments, near monolayer amounts of polymer (one or a few monolayers) covalently attached to the porous surface of the silica gel minimize self-quenching from polymer-polymer interactions, thereby allowing for improved luminescence, as well as more complete analyte-fluorophore interaction, which in turn has the ability to lower detection limits. Because silica gel is a chromatographic support, mixtures of explosives can be simultaneously separated into their individual components.

Figure 1B:
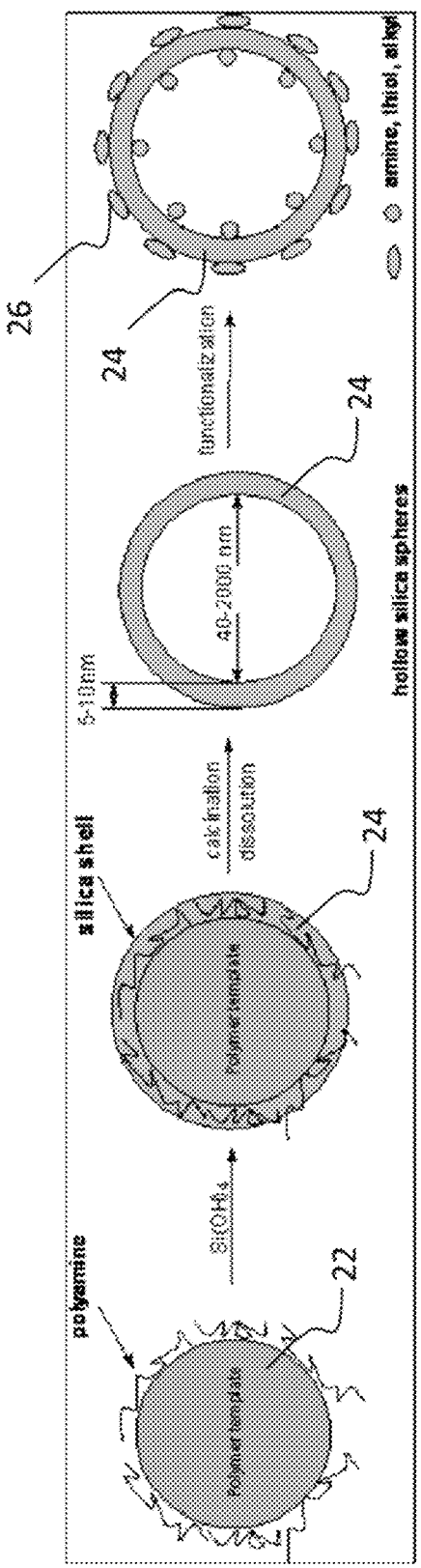
FIG. 1B is a schematic representation of a process for forming a sensor and a sensor with a chromatographic silica support according to a preferred embodiment of the invention.

FIG. 1B illustrates a method for forming a silica nanoparticle based to sensor of the invention. The method begins with a polymer nanoparticle template 22 that is treated with polyamine. A silica shell 24 is then formed from $Si(OH)_4$ and when the polymer template is removed a hollow nanoparticle sphere nanoparticle typically has dimensions of about 20-200 nm and shell thickness of about 5-10 nm. The particle is then functionalized with copolymers of silafluorene and fluorene 26 to complete the sensor that, as shown in the experimental details below is a highly sensitive high explosive sensor in solution. Details of formation of the hollow silica nanoparticles can be found on US Patent Publication US 20110229576 (U.S. application Ser. No. 12/673,224) entitled "Hollow Silica Nanospheres and Methods of Making the Same".

Example fluorescent polymers that can be used in a sensor and sensing method of the invention include fluorescent organosilicon polymers, e.g., the luminescent organosilicon copolymers:
PSFS—poly(silafluorenyldiethynylspirobifluorene);
PSFF—poly(silafluorenyldiethynylfluorenyl) and
PSS—poly(silolediethynylspirobifluorene).

PSS is a new polymer where chloroplatinic acid is used a catalyst to facilitate hydrosilation, while PSFS and PSFF are prepared according to known methods, with a modifying capping procedure. Rather than capping the terminal alkynes by hydrosilation with dimethylphenylsilane, the polymers were capped by hydrosilation with trimethoxysilane. This provides a reactive end group for covalent attachment to a silica surface.

Preferred polysilole copolymers can be made in fewer than seven steps, which translates into a low cost sensor that can be easily produced. This also allows the sensor to be considered disposable and since the sensor needs very little equipment, it lends itself to being highly useful as portable field sensor. The cap allows the polymers to be easily covalently attached to silica surfaces. The polymers are characterized as the dimethylphenylsilane capped polymer, since the reactive trimethoxysilane cap could easily react with glass in an NMR tube or to silica in a GPC column. In general, the capped polymers can be attached to any silica surface.

Experiments were conducted to demonstrate embodiments of the invention. Artisans will recognize additional features and aspects of the invention from the following discussion of experiments that were conducted.

The experiments demonstrated the covalent surface attachment of polymers containing silole and silafluorene moieties on TLC substrates. The formed sensors were demonstrated to have improved detection sensitivity as compared to thicker spray coated films, as well as allow the separation of explosive mixtures. The differing chromatographic retention times allow a preliminary identification of explosive type, which provides functionality for a simple field test kit for the identification of subnanogram traces of explosive residues.

Experimental Data

Chromatographic Support

Materials Preparation

Synthesis of 5H-dibenzo[b,d]silole 3.00 g (9.62 mmol) of 2,2'-dibromobiphenyl were dissolved in 35 mL of freshly distilled (under $N_2$ from sodiumbenzophenone ketyl) THF. The reaction temperature was reduced to −52° C. at which point 13.25 mL of 1.6 M n-butyl lithium in hexanes were added dropwise and warmed slowly to room temperature, while stirring overnight under an argon atmosphere. The reaction was cooled again to −52° C. and 12.1 mL (28.8 mmol) of a 25% (V/V) solution of dichlorosilane in xylene was added dropwise. The reaction was allowed to stir for 1 hr, warmed to room temperature and stirred an additional hour under Ar. The reaction was quenched with 25 mL of 10% ammonium chloride and extracted with diethyl ether. Purification was accomplished by vacuum distillation at 100° C. at $10^{-3}$ torr. If further purification was needed, distillation can be repeated. This yielded a clear, colorless liquid (1.1 g 63%). $^1$H NMR (400 MHz, $CDCl_3$): δ 7.85 d (2H), δ 7.30 d (2H), δ 7.46-0.21 m to (4H), δ 4.72 s (2H).

Synthesis of 2,3,4,5-tetraphenyl-1H-silole 9.00 g (50.5 mmol) of diphenylacetylene were dissolved in 75 mL of freshly distilled diethyl ether. Then 0.88 g (126.2 mmol) of Li wire, cut into 2-3 mm pieces was added and the mixture stirred under an argon atmosphere for 4 hr, or until the reaction had turned a reddish/brown color with a significant amount of precipitate. Under a heavy Ar flow the unreacted pieces of lithium were removed with the use of a spatula. The reaction was frozen in a liquid $N_2$ bath for 30 min. At this point 21 mL (50.5 mmol) of a 25% by volume solution of dichlorosilane in xylene was added dropwise. The reaction was warmed slowly to room temperature and stirred under an argon atmosphere for 3 hr. The solvent was removed and the mixture dissolved in toluene and extracted, three times with brine in a separator funnel. The organic layer was dried over MgSO$_4$ and the volume was reduced under vacuum and left to crystallize. This yielded bright, yellow crystals (5.9 g, 59%). Mp: 205-206° C. (lit. 209-210° C.).[77] 1-1 NMR (400 MHz, CDCl$_3$): δ 6.80-6.85 and 7.00-7.24 (br m, 20H, Ph), 4.90 (s, 2H, SiH$_2$). $^{13}$C{H} NMR (100 MHz, CDCl$_3$): δ 157.50, 138.74, 135.20, 131.63, 129.62, 129.36, 128.09, 127.72, 126.63, 126.23. IR (KBr): Si—H 2140 cm$^{-1}$.

Synthesis of Poly(silafluorenyldiethynylspirobifluorene)

Both 29 mg (0.16 mmol) of 5H-dibenzo[b,d]silole and 58 mg (0.16 mmol) of 2,7-diethynyl-9,9'-spirobi[fluorene] were put into a round bottom flask equipped with a condenser. A catalytic amount (~4 mg) of H$_2$PtCl$_6$ was added under an argon atmosphere along with 1.5 mL of dry toluene. The reaction was stirred at 60° C. for 36 hr. The temperature was reduced to 35° C. and an excess (50 μL) of dimethylphenylsilane was added and stirring continued for an additional 2 hr. The H$_2$PtCl$_6$ was removed by filtration through filter paper and toluene was removed by vacuum evaporation. The resulting brownish/yellow oil was dissolved in 1 mL of THF and added to 10 mL of stirring methanol to precipitate the polymer. This process was repeated two times and gave a pale yellow solid. GPC: 13 kDa, PDI 1.3.

Synthesis of Poly(tetraphenylsiloilediethynylspirobifluorene)

Both 50 mg (0.13 mmol) of 2,3,4,5-tetraphenyl-1H-silole and 48 mg (0.13 mmol) of 2,7-diethynyl-9,9'-spirobi[fluorene] were put into a flask equipped with a condenser. A catalytic amount (~4 mg) of H$_2$PtCl$_6$ was added under an argon atmosphere, followed by 1.5 mL of dry toluene. The reaction was stirred under Ar at 60° C. for 36 hr. The temperature was reduced to 35° C. and an excess (50 of dimethylphenylsilane was added and stirring continued for 2 hr. The H$_2$PtCl$_6$ was removed by filtration and toluene was removed under vacuum. The resulting brownish-yellow oil was dissolved in 1 mL of THF and added to 10 mL of stirring methanol to precipitate polymer. This was repeated two times and yielded a pale yellow solid. GPC: 26 kDa, PDI 1.2.

Preparation of Trimethoxysilane Capped PSS and PSFS—

Trimethoxysilane capped polymers were prepared in the same fashion as the dimethylphenylsilyl capped polymers. Trimethoxysilane was used in place of the dimethylphenylsilane in the hydrosilation steps above, and the polymers were precipitated using a 1:10 chloroform:hexanes mixture.

TLC Surface Functionalization—

Standard TLC silica gel 60 plates on aluminum backing were used. Large plates were cut into slides approximately 5 cm (H)×1.5 cm (W). The TLC plates were soaked in the polymer solution, which consisted of 1 mg of the polymer dissolved in a 20 mL solution of a 1:1 mixture of toluene:THF, for approximately 2 min. The slides were put into a 50/50 volume solution of THF/methanol to remove the non-covalently adsorbed polymer. This process was repeated two more times. After the last washing step the TLC plates were allowed to dry in a desiccator. The TLC plates were stored in a vacuum desiccator, where they were protected from oxygen and light until use.

Explosive Detection Testing—

Detection limits were measured using an observer independent from the random spotter in order to have a double blind study. Known amounts of analyte and solvent blanks were deposited randomly onto the TLC plate in multiple lanes using a standard micropipette. After solvent evaporated, the TLC plates were illuminated using a 360 nm handheld UV lamp. The observer was asked to determine where they could see areas of fluorescence quenching. Detection limits are the last clearly distinguishable quenching spot, as viewed by the observer. All tests were run in triplicate, and five different observers were used.

Explosive Materials—

Some purchased explosive standards were dilute solutions to eliminate the explosion hazard. All synthetic manipulations were carried out under an atmosphere of dry argon gas using standard Schlenk techniques. Dry solvents were purchased from Aldrich Chemical Co. Inc. and used after purification with an MBraun MB Auto Solvent Purification System. Spectroscopic grade THF from Fisher Scientific was used for the fluorescence measurements. All other reagents were purchased from Aldrich Chemical Co. and used as received. Picric acid and DNT were purchased from Aldrich Chemical Co. and recrystallized from ethanol and methanol, respectively. TNT was prepared in small quantities from DNT and recrystallized from toluene. RDX, HMX, Tetryl, TNG and PETN were purchased as 1 mg/mL analytical standards in acetonitrile from Cerilliant®.

NMR spectral data were collected with Varian Unity 400 or 500 MHz spectrometers (400 MHz for $^1$H, 100 MHz for $^{13}$C, and 99.4 MHz for $^{29}$Si NMR). GPC-RI data were obtained with the use of a Viscotek GPCmax VE 2001 GPC and a Viscotek VE 3580 refractive index detector calibrated with polystyrene standards. Fluorescence emission and excitation spectra were recorded with the use of a Perkin-Elmer Luminescence Spectrometer LS 45. UV-vis spectra were obtained with the use of a Perkin-Elmer Lamda35 UV/Vis spectrometer.

Sensor Fabrication and Testing

The PSFF and PSFS polymers shown in FIGS. 3A and 3B were prepared as described and shown in FIGS. 2A and 2B above according to modified known procedures, but rather than capping the terminal alkynes by hydrosilation with dimethylphenylsilane, the polymers were capped by hydrosilation with trimethoxysilane. This provides a reactive end group for covalent attachment to a silica surface. Polymer molecular weights were characterized as the unreactive dimethylphenylsilane capped polymer, since the trimethoxysilane cap reacts with glass, trace moisture, and may self-polymerize further in a gel permeation chromatography (GPC) column.

The PSS polymer shown in FIG. 3C is a new polymer prepared as described above. Its peak emission is at 470 nm in solution and 485 nm in the solid state. The molecular weight (MW) measured by GPC is 26 kDa, with a polydispersity index (PDI) of 1.3. The polymer exhibits aggregation-enhanced emission, as expected for compounds that contain the tetraphenylsilole moiety. This has been previously attributed to freezing out rotation of the phenyl rings in the solid state, thereby decreasing the predominant nonradiative decay pathways.

PSFS and PSS were covalently linked onto non-fluorescent silica TLC plates using the condensation reaction of the surface hydroxides of the silica with the trimethoxysilyl cap of the polymer. Nitroaromatic compounds were easily resolved into individual components on the treated TLC plates using common organic solvent mixtures as eluants.

Surface attachment was done by taking a solution of the trimethoxysilane capped polymers (98% THF:1% methanol:1% toluene) and submerging the TLC plate into the solution. This was followed by washing the unreacted polymers by submerging the TLC plate into a solution of 50:50 THF/methanol. The washing process was repeated three times and the TLC plates were stored in a desiccator or an amber bottle until use. The surface coating is uniform and yields an even, bright surface.

Figure 4:
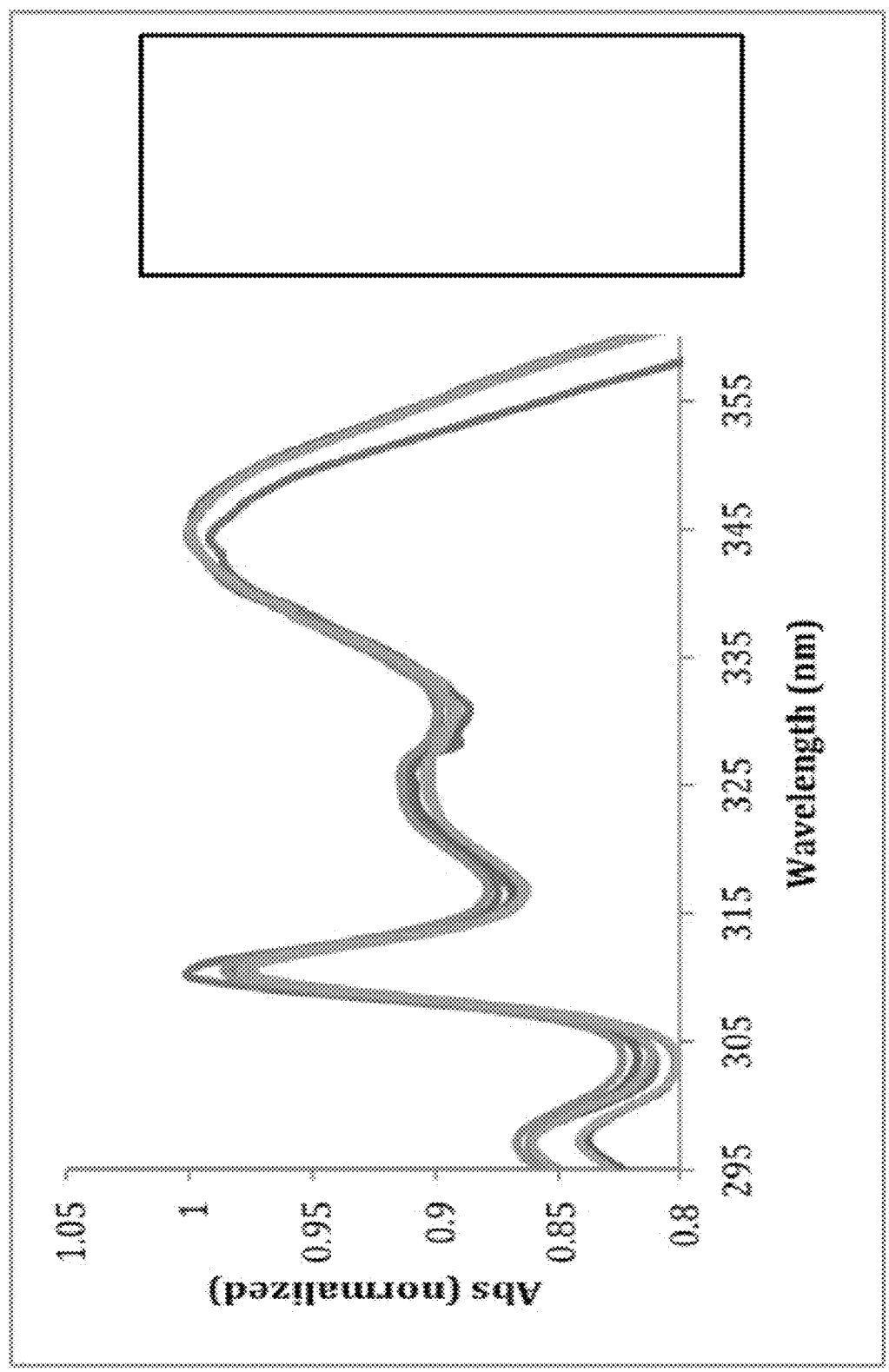
FIG. 4 is a plot showing UV/vis spectra taken of solution aliquots taken during the coating process of 20 sensors with 0.025 mg/mL poly(tetraphenyl-silolediethynyl-spirobifluorene) (PSS)
Figure 5A:
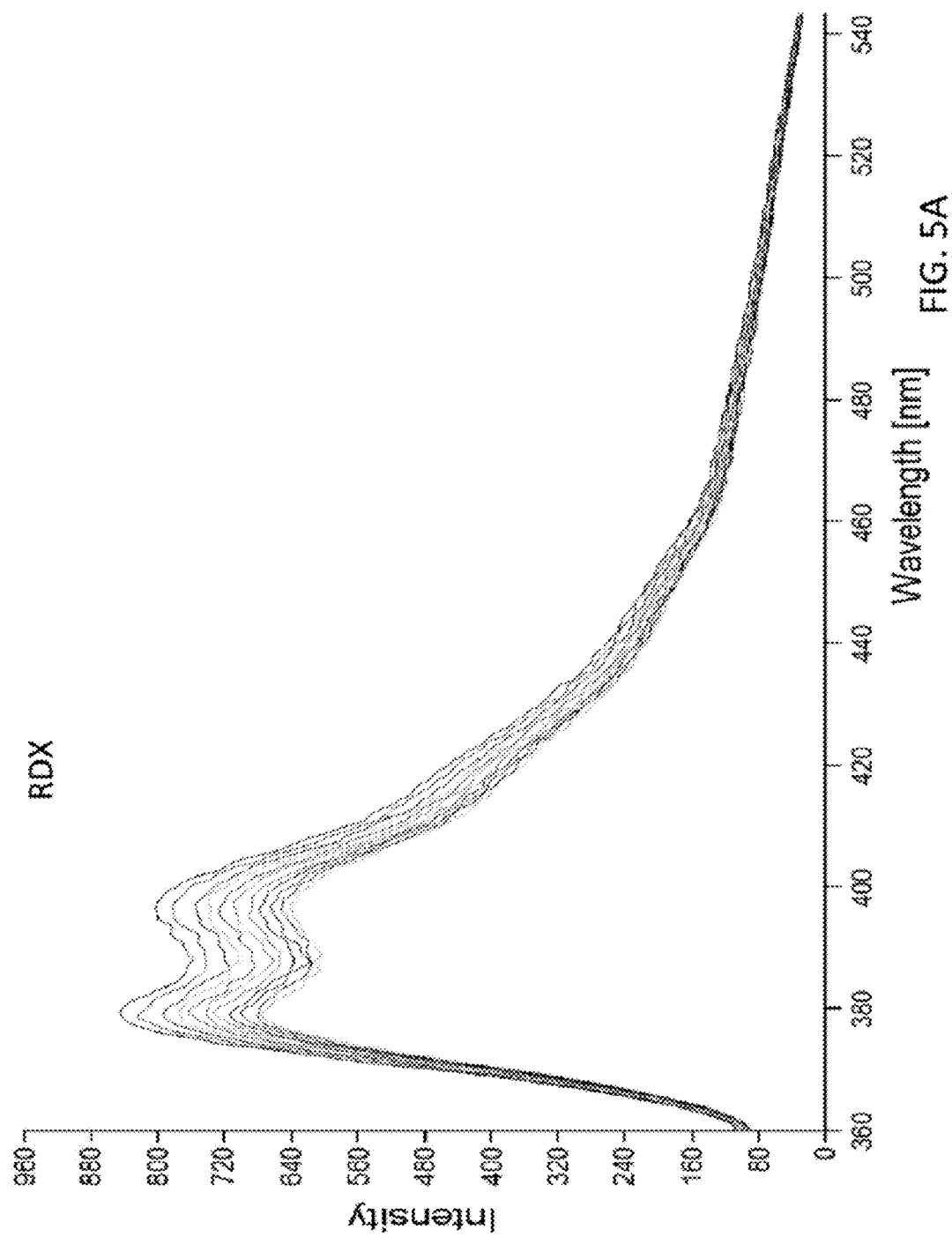
FIGS. 5A-5D show the fluorescence quenching spectra of PSS with added explosive, respectively: RDX, HMX, CL-20, and PETN.
Figure 5B:
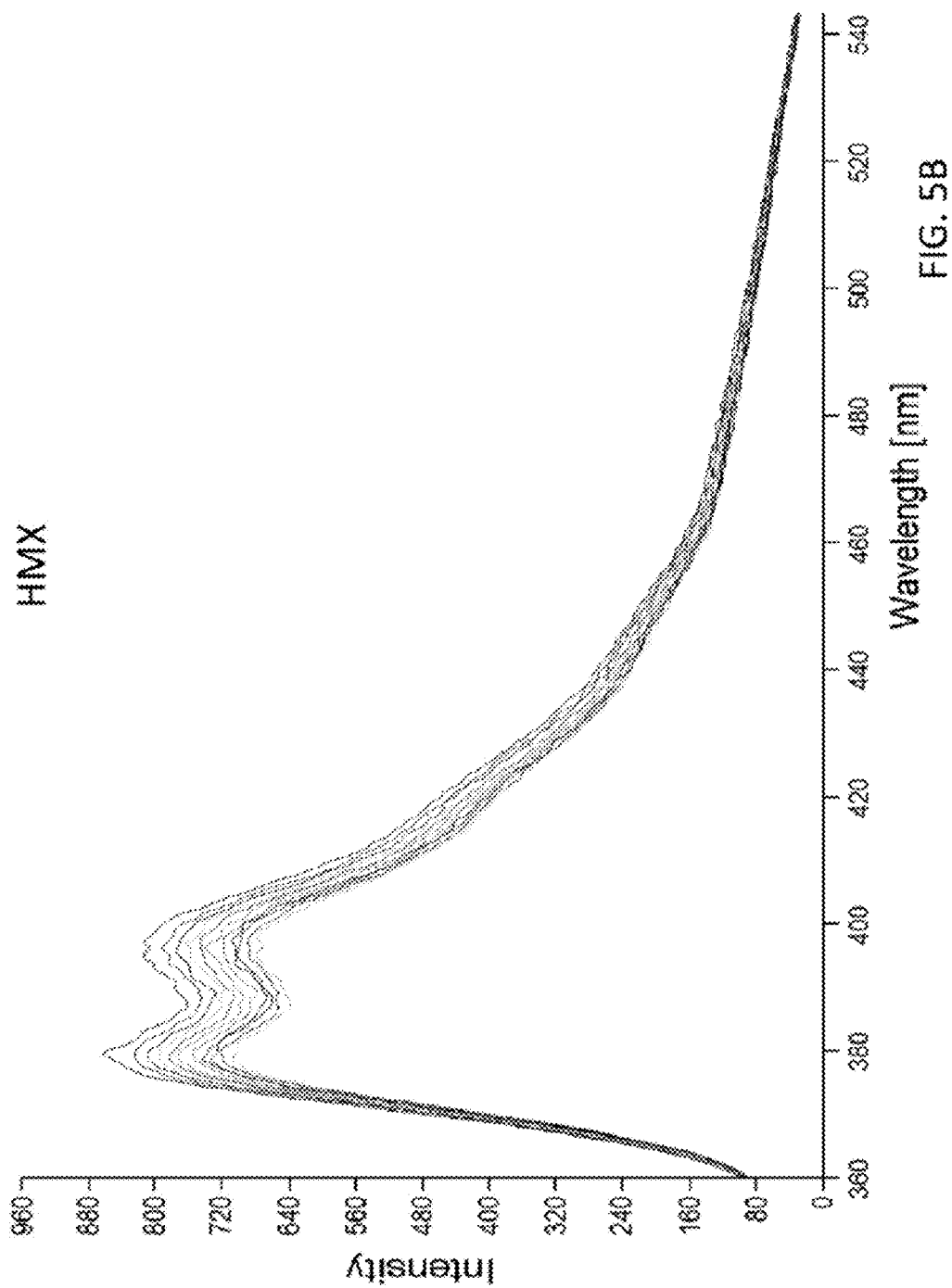
Figure 5C:
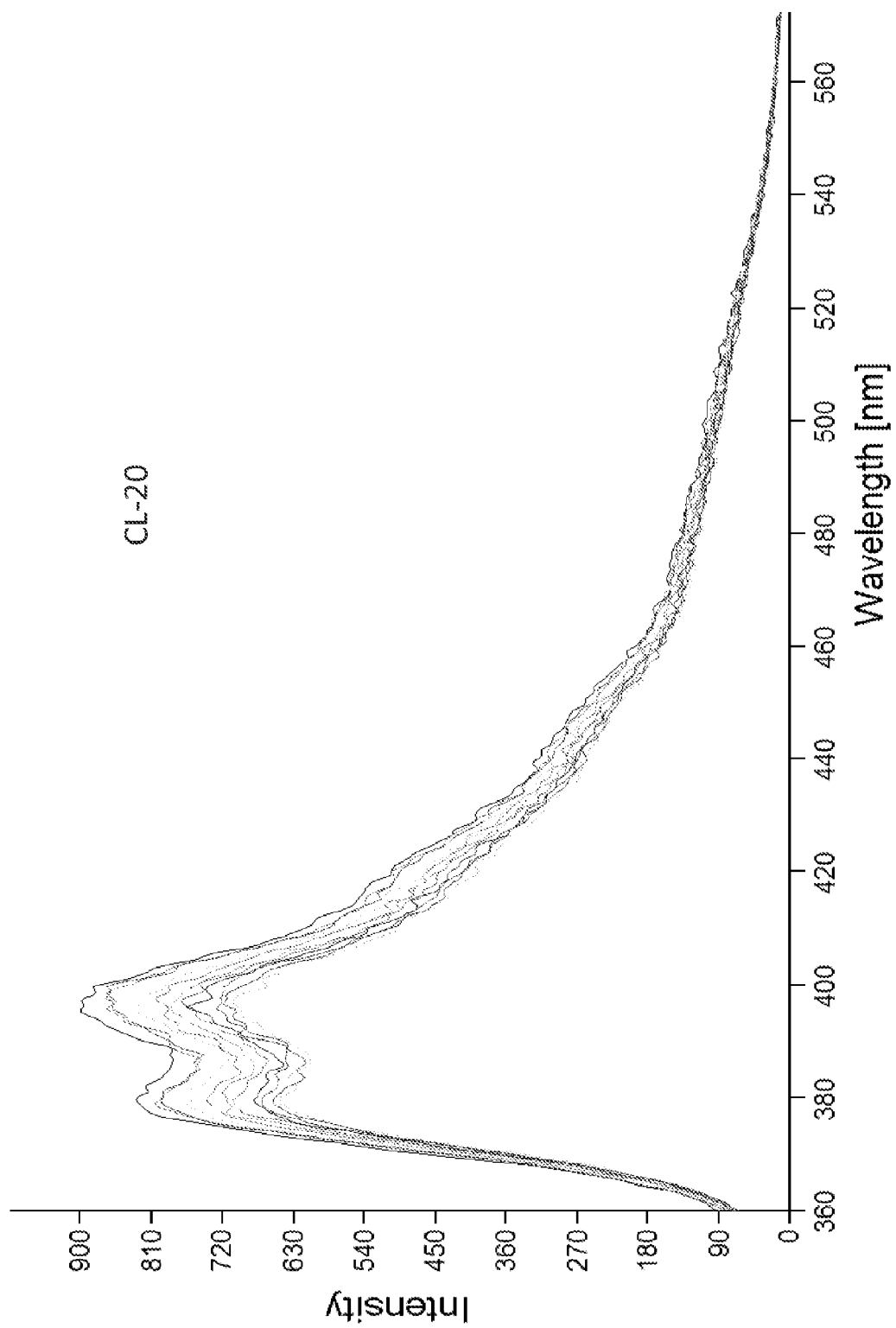
Figure 5D:
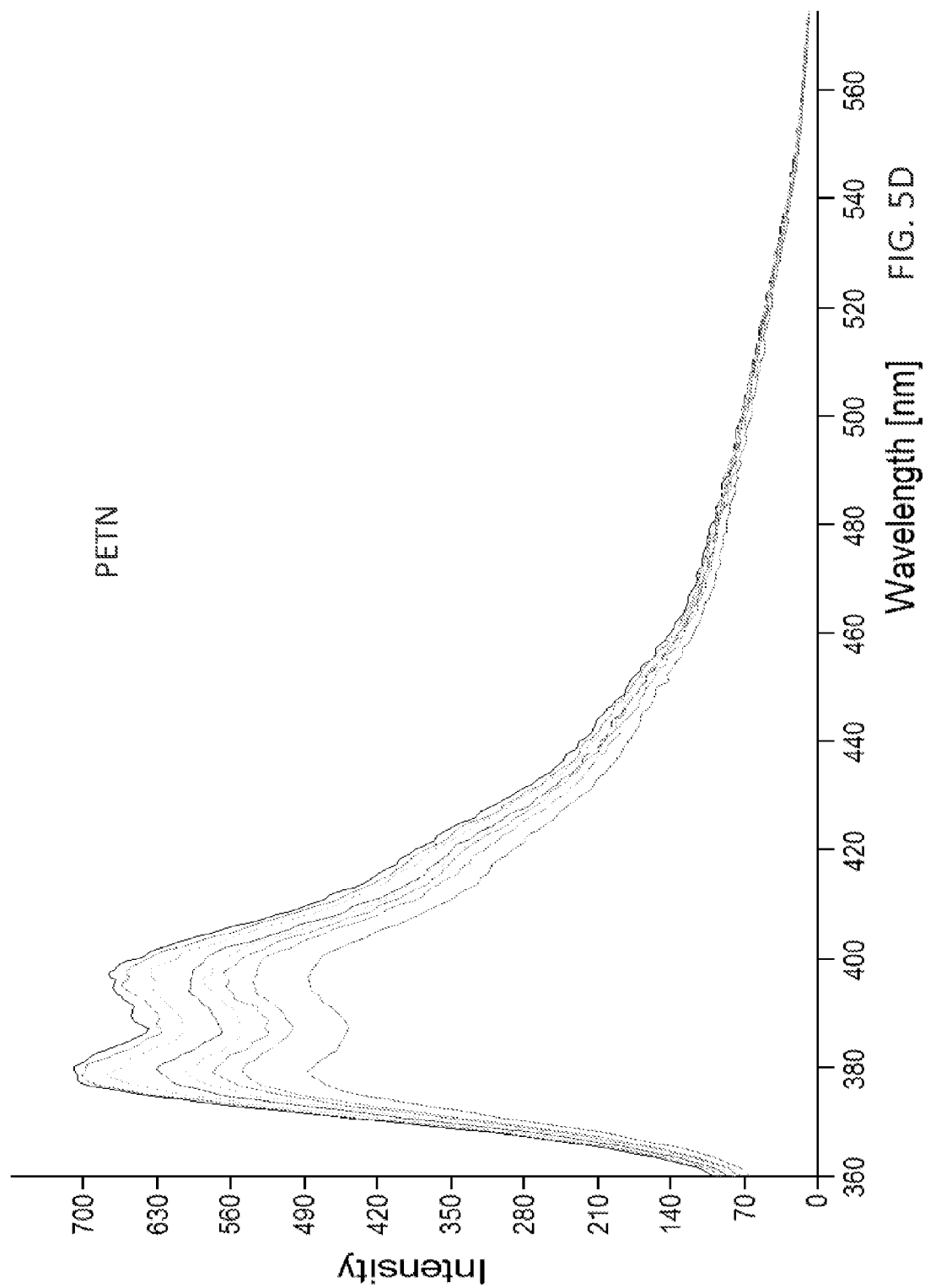

The small amount of fluorophore removed from solution by coating twenty TLC plates in a 0.025 mg/mL polymer solution in toluene was measured. Every four TLC coatings, a 1-mL aliquot was removed from the coating solution and analyzed by UV/vis. FIG. 4 shows the spectra of 20 solution aliquots with PSS from a solution coating process that used 0.025 mg/ml. The spectra show that there is a barely detectable difference in the absorbances of the aliquots measured between each group of coatings. The slight difference between the non-coated TLC solution and the aliquot of the twentieth TLC group was used to estimate an upper limit on the amount of PSS fluorophore that deposited during surface coating. Using the average difference in absorbance at 311 and 325 nm a concentration for the amount of polymer removed from solution during coating of the twenty TLC plates could be estimated as at most ~350 ng fluorophore per TLC plate. It seemed remarkable that such a small amount of fluorescent polymer was providing a bright photoluminescence that was observed in the detection studies.

To test whether the estimated 350 ng of polymer could reasonably produce adequate fluorescence emission, a 100-μl solution was prepared (by dilution) containing 350 ng of PSS and delivered onto a TLC plate by multiple spotting. Photoluminescence of the spot-coated TLC plate demonstrated that only 350 ng of fluorophore mass loaded onto a TLC plate provides bright luminescence. This qualitative approach was adopted because of the difficulty in coating a single TLC plate with a very dilute solution so a significant decrease in fluorophore concentration occurred. Due to the slow kinetics of the concentration dependent surface coating reaction, very dilute solutions of the trimethoxyl capped fluorophore could not be used for the coating process in a reasonable period of time.

Figure 6C:
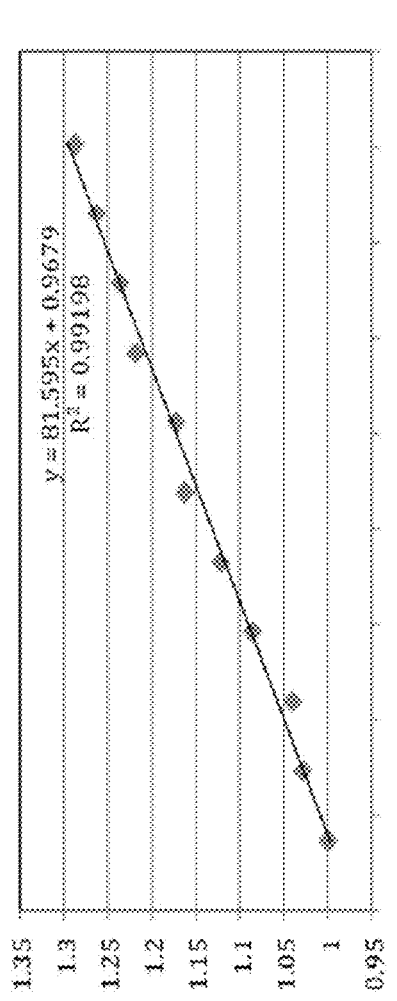
Figure 6D:
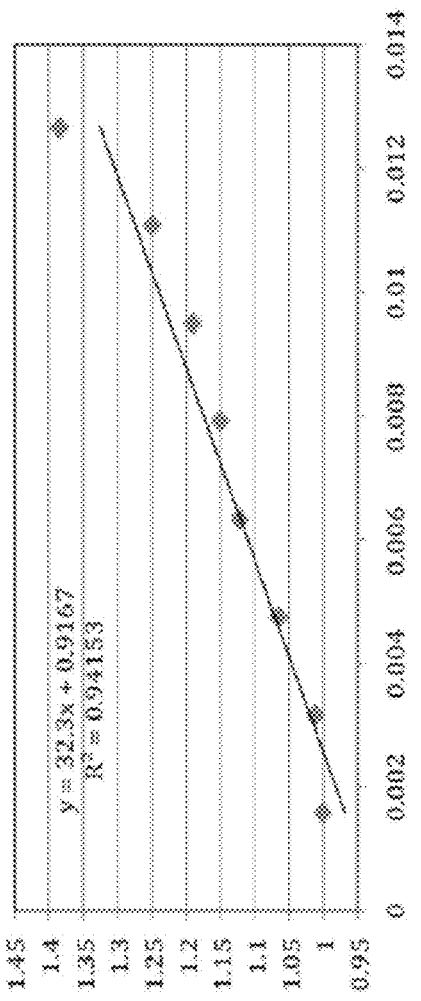

In solution, there is weak coordination between the nitro group on the explosive and the silicon atom of the metallole fragment. See, e.g., J. C. Sanchez et al., "Lewis acid-base interactions enhance explosives sensing in silacycle polymers," Anal. Bioanal. Chem., 395(2), 387-392 (2009). Therefore, only a small amount of quenching is seen in solution for the additions of RDX, HMX, CL-20, and PETN to PSS with small Stem-Volmer constants determined (Table 1). FIGS. 5A-5D show the fluorescence quenching spectra of PSS with added explosive, specifically: RDX, HMX, CL-20, and PETN. The spectra for RDX, HMX, and CL-20 were measured in cyclohexane and that for PETN was measured in acetone. FIGS. 6A-6D show the Stern-volmer quenching plots with the explosives: RDX, HMX, CL-20, and PETN in cyclohexanone and acetone (PETN) solvents, respectively. The FIG. 6 plots were generated from the FIG. 5 data. All the experimentally determined Stern-Volmer quenching Constants are orders of magnitude lower than the values determined previously for nitroaromatics. See, S. J. Toal and W. C. Trogler, "Polymer sensors for nitroaromatic explosives detection," J. Mater. Chem., 16, 2871-2883 (2006); J. C. Sanchez and W. C. Trogler, "Efficient blue-emitting silafluorene-fluorene-conjugated copolymers: selective turn-off/turn-on detection of explosives," J. Mater. Chem., 18, 3143-3156 (2008); J. C. Sanchez, S. A. Urbas, S. J. Toal, A. G. DiPasquale, A. L. Rheingold and W. C. Trogler, Macromolecules, "Catalytic Hydrosilylation Routes to Divinylbenzene Bridged Silole and Silafluorene Polymers. Applications to Surface Imaging of Explosive Particulates," 2008, 41, 1237-1245; S. J. Toal, D. Magde, W. C. Trogler, "Luminescent Oligo(tetraphenyl)silole Nanoparticles as Chemical Sensors for Aqueous TNT,"Chem. Commun., 5465 (2005); R. E. Dugan, W. C. Trogler, "Visual Detection of Trace Nitroaromatic Explosive Residue Using Photoluminescent Metallole-Containing Polymers, S. J. Toal; J. C. Sanchez," J. Forensic Sci., 52, 79-83 (2007).

The $K_{SV}$ constants in Table 1 are provided along with some published $K_{SV}$ constants (J. Yinon, "Field detection and monitoring of explosives." Trends Anal. Chem., 21, 292-301 (2002)) for comparison with quenching efficiency by nitroaromatic compounds. The experimentally determined Stern-Volmer quenching constants for non-nitroaromatic explosives are much lower than the values for TNT, DNT, and PA.

TABLE 1

Summary of Stern-Volmer constants ($K_{SV}$) for quenching of the photoluminescence of poly(silafluorenyldiethnylspirobifluorene)

| Explosives | $K_{sv}(M^{-1})$ | Explosives | $K_{sv}(M^{-1})$ |
| --- | --- | --- | --- |
| RDX | 11.2 | HMX | 12.1 |
| PETN | 32.3 | Cl-20 | 81.6 |
| TNT | 10300 | DNT | 4300. |
| Picric acid | 14300 | | |

Although quenching is inefficient for non-nitroaromatic explosives in solution, strong quenching occurs on fluorophore coated TLC plates after solvent evaporation. There are several potential reasons for inefficient quenching by non-nitroaromatic explosives in solution. Charge transfer π-complex formation between nitroaromatic explosives and the aromatic silole or silafluorene moieties (either in the ground or excited state) may enhance association-quenching in solution as compared to non-nitroaromatic quenchers. The excited states of the nitroaromatic explosives also lie at lower energies, which would be expected to enhance the rate of electron transfer quenching. Finally, the greater spatial extent of the delocalized nitroaromatic π electron system should enhance the probability of electron transfer during collisions in solution.

The evaporation of solvent removes the mobility of analyte and fluorophore, causing the two to be in close proximity, thereby dramatically improving quenching efficiencies in the solid state. Explosive detection with surface anchored fluorophores was done in two ways. Nitroaromatic compounds, which are mobile on the TLC substrate, can be spotted at the bottom of the plate in a similar manner as in a thin layer chromatographic separation. The plate is developed using common organic solvents to separate the mixture. A mixture of nitroaromatics in a sample was demonstrated to be easily separated to reveal the individual components and identify them by comparison with standards.

Specifically, DNT a common byproduct of manufacturing TNT, was separated from TNT along with picric acid and tetryl using a solvent mixture of dichloromethane: hexanes. Separation of RDX from HMX was performed using a solvent mixture of 15:1, toluene to isopropanol. Both RDX and HMX are nitramine type high explosives used in compound explosives The separation was clearly on the TLC plate sensor of the invention, which were coated with the trimethoxysilyl capped PSS.

The testing used dilute explosive solutions ranging from 500 ng/mm² to 50 ng/mm² on a single TLC sensor plate of the invention and the levels of 50 ng for RDX, HMX, PETN, and Tetryl were easily observed. All initial explosive spots were detectable in the picogram range down to the 50 ng/mm² level. Visual detection limits were obtained using a double blind method where the observer determined detection spots after an independent person randomly spotted various explosives, concentrations, and solvent blanks on substrates. Table 2 shows a summary of the detection limits observed using both PSS and PSFS coated TLC plates. As seen in previous applications of polysilole polymers, the nitroaromatics are detected at the lowest levels. Nitramines and nitrate ester detection limits are often an order of magnitude higher (Table 2). PSS is an efficient green emitter, which is more easily seen by an observer and generally provides lower detection limits as shown in the table. Overall, the data shows that PSFS and PSS sensors of the invention with a near monolayer on a TLC support provide

TABLE 2

Summary of visual explosives detection limits.

| PSS TLC plate detection limits | | PSFS TLC plate detection limits | |
|---|---|---|---|
| Explosive | (Mass/area) | Explosive | (Mass/area) |
| TNT | 4.5 pg/mm$^2$ | TNT | 4.5 pg/mm$^2$ |
| DNT | 4.5 pg/mm$^2$ | DNT | 4.5 pg/mm$^2$ |
| PA | 4 pg/mm$^2$ | PA | 4 pg/mm$^2$ |
| Tetryl | 45 pg/mm$^2$ | Tetryl | 450 pg/mm$^2$ |
| HMX | 25 pg/mm$^2$ | HMX | 45 pg/mm$^2$ |
| RDX | 45 pg/mm$^2$ | RDX | 450 pg/mm$^2$ |
| PETN | 450 pg/mm$^2$ | PETN | 450 pg/mm$^2$ |
| CL-20 | 750 pg/mm$^2$ | CL-20 | 1500 pg/mm$^2$ |

Experimental Data

Silica Nanoparticle

Silica nanoparticles were coated with a blue emitting silafluorene-fluorene polymer, poly(silafluorene-(9,9-dimethyl-9Hfluorene)divinylene) (PSFF, 1) and tested as a chemosensor for the detection of aqueous solutions of TNT and RDX. PSFF is an alternating silafluorene-fluorene copolymer conjugated through divinylphenylene bridges as described above and can be synthesized as described above or previously described in the literatures. Hollow silica nanoparticles with a diameter of ~100 nm were fabricated by the sol-gel reaction with polystyrene latex spheres as template, which are then removed by calcination. In experiments, uniform 85 nm diameter hollow silica nanoshells produced have a porous wall about 10 nm thick and exhibit a large surface area (400 m$^2$g$^{-1}$ by BET measurement). In summary, the template synthesis uses 100 nm beads to make them in the sol-gel template reaction and then after they are calcined and they shrink to 85 nm when the template is removed.

Three methods were used to coat PSFF onto the silica nanoparticles. The first was stirring the NPs in a toluene solution of PSFF and allowing the polymer to adsorb to the mesoporous silica surface.

EXPERIMENTAL

Octadecyl Group and PSFF Polymers on Hollow Silica NPs

Coating of PSFF on Plain Hollow Silica NPs.—

3 mg of silica NPs were suspended in 0.3 mL toluene and 0.3 mg of PSFF was added the suspension and mixture was stirred 4 hours before spinning down the NPs and washed by toluene, ethanol and water successively. The PSFF coated NPs were resuspended in 3 mL of pH7.4 PBS for explosive detection.

Coating of Silane-PSFF.

The procedure for coating silane-PSFF on plain silica Nps 61 was same as coating of PSFF except that absorption time was 8 hours.

Coating of Octadecyl.—

Octadecyl groups coating on plain hollow silica Nps was accomplished by using 3 mg of silica NPs, suspended in 1 mL of toluene followed by the addition of 60 uL of octadecyl (triethoxy)silane. The mixture was then let to stir overnight at room temperature. After washing with toluene the NPs were coated with PSFF with the same procedure of coating PSFF on plain silica NPs. Additional details can be found in Trogler et al., "Hollow Silica Nanospheres Containing a Silafluorene-Fluorene Conjugated Polymer for Aqueous TNT and RDX Detection," W.C. Chem. Commun., 2010, 46, 6804-6804. The second method introduced a covalent bond between PSFF and the surface of silica nanoparticles in a manner similar to those described above with respect to TLC plates, specifically by reaction of a trimethoxysilyl-capped PSFF and silica nanospheres in toluene. The trimethoxysilyl group was introduced at the end of the polymer chains by catalytic hydrosilation of the terminal chain alkyne groups with trimethoxysilane. A third method of functionalization employed octadecyl modified silica silicon nanoparticles as the support for adsorbed PSFF. Octadecyl groups were grafted on silica nanoparticles by reacting octadecyl(triethoxy)silane and the hollow silica nanoparticles in toluene solution. Then PSFF was adsorbed to the $C_{18}$ modified silica NPs in toluene. The mass ratios of loaded PSFF and silica NPs are 51:1000, 35:1000 and 18:1000, respectively, for PSFF, silane-PSFF, and PSFF coated $C_{18}$ modified silica nanoparticles, respectively.

The PSFF has a relatively high average molecular weight of 26 000 Da (GPC analysis vs. polystyrene standards). In the first coating method, it is likely that the PSFF chains are physisorbed from solution and trapped in the porous structure of the bare silica nanoparticles. It is also likely that some polymer chains penetrate the porous wall and adsorb to the inner surfaces of the nanoparticles. In the covalent attachment method, when silane-PSFF was coated on silica nanoparticles the reaction with surface Si—OH groups occurs simultaneously with any adsorption, and appears to limit the amount of polymer taken up by the porous nanoshells. Covalent surface attachment of PSFF appears to decrease the porosity of the silica shell and partially block the absorption of additional polymer within the pores and core of the nanoparticles. Similarly, the covalently anchored $C_{18}$ layer also could decrease the effective pore size and available surface of the silica shell, which also explains why less PSFF can be physisorbed on the hydrophobic $C_{18}$ modified nanoparticles. The zeta potential of $C_{18}$ modified nanoparticles decreases dramatically from −25 mV to −15 mV. This is a result of the covalent attachment of the trimethoxysilyl groups by reaction with the surface hydroxide groups that impart the nanoparticles with a negative zeta potential. The reduced zeta potential of $C_{18}$ nanoparticles after PSFF coating suggests that the relatively large amount of adsorbed PSFF further shields the surface charge.

Hollow silica nanoparticles posses a negatively charged surface with a zeta potential of −25 mV (See, Table 3 below). These nanoparticles can be resuspended in a pH 7.4 PBS (phosphate buffered saline) and dynamic light scattering analysis (DLS) reveals an average size to be 185±45 nm. After the C18 coating, their size increases slightly (220±65 nm) and the zeta potential decreases to −15 mV. Increased aggregation of the silica nanoparticles in solution is attributable to the hydrophobic surface layer and the reduced zeta potential.

Figure 7B:
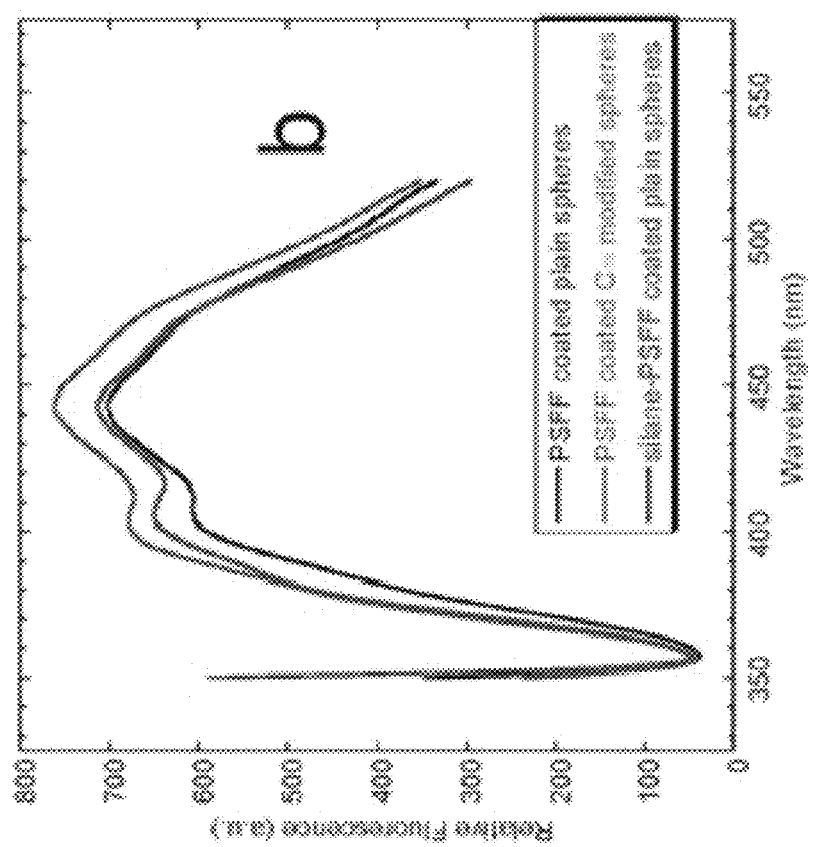
FIGS. 7A-7B show absorption and photoemission spectra of PSFF coated silicon nanoparticles in a phosphate buffer solution.
Figure 7A:
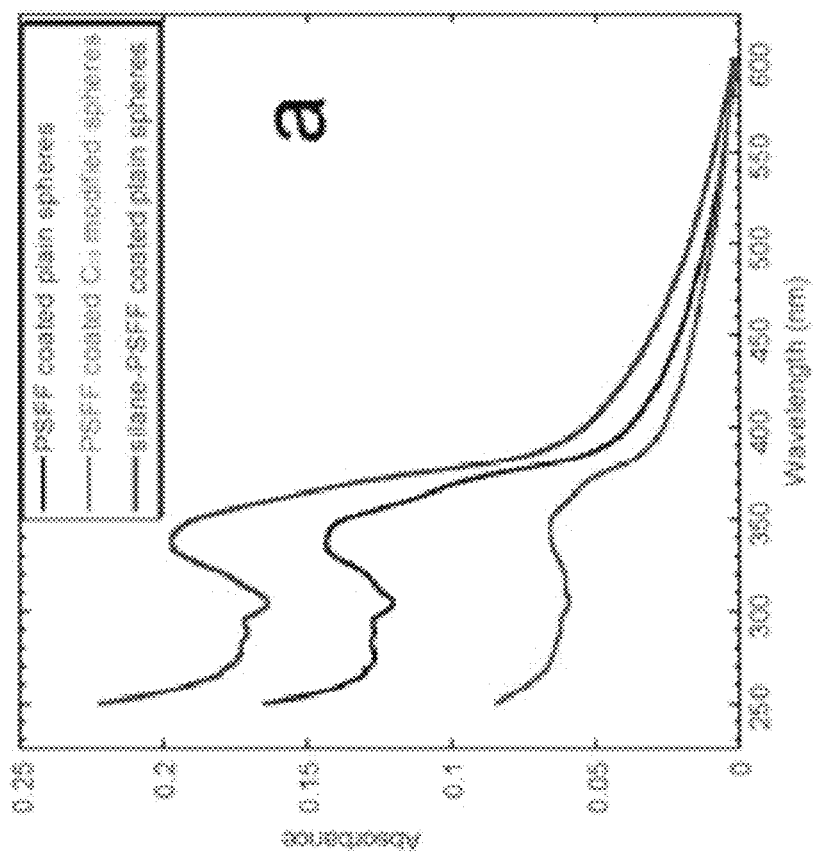

FIGS. 7A and 7B shows the absorption and emission spectra of PSFF coated silica nanoparticles in a PBS suspension. Free PSFF in toluene solution has a maximal absorption at 341 nm and a broad emission at 385 nm. PSFF coated silica nanoparticles in PBS have a similar absorption wavelength, but show increased absorbance at higher energy that can be attributed to scattering by silica nanoparticles. The emission of the nanoparticles are red shifted and broader when compared to the free polymer in toluene, which resembles the PSFF in the solid state. While the mechanism is not exactly understood or necessary to practice the invention, a possible explanation is that the $C_{18}$ creates a more hydrophobic environment, which may predispose the nanoparticles to adsorb longer polymer chains. Self-aggregation also causes the polymer emission to broaden from the various conformers present in the solid state as well as from excimer formation.

TABLE 3

Sizes and zeta potentials of silica NPs

| | Plain NPs | $C_{18}$ modified NPs | PSFF coated $C_{18}$ modified NPs | PSFF coated NPs | Silane-PSFF coated NPs |
|---|---|---|---|---|---|
| Size/nm | 185 ± 45 | 220 ± 65 | 255 ± 45 | 290 ± 50 | 275 ± 60 |
| Zeta potential/mV | −25.0 | −15.0 | −1.0 | −1.5 | −5.5 |

Relative quantum yields of PSFF coated silica NPs in PBS suspension were calculated using the equation below:

$$\Phi_x = \frac{A_r}{A_x}\left(\frac{n_x^2}{n_r^2}\right)\Phi_r \int \frac{E_{mx}}{E_{mr}}$$

The fluorophore reference used was 9,10-diphenylanthracene. In the equation, $A_r$ is the absorption of the reference and $A_x$ is the absorption for fluorophore. $E_{mr}$ and $E_{mx}$ are the total area under the emission plot of the reference (r) and fluorophore (x). $n_x$ and $n_r$ are the indices of refraction for the solvents being used.

Table 4 shows that silane capped PSFF coated silica nanoparticles exhibit the highest quantum yield of 0.13 and the PSFF coated plain nanoparticles have a quantum yield as low as 0.044. The values inversely correlate with the amount of polymer loading. A close distance between polymer chains promotes excimer formation and emission quenching. The data suggest that the covalently anchored PSFF coated nanoparticles have the best balance of AIE (aggregation induced emission) due to restricted rotation in the surface constrained polymer, yet providing enough separation between the polymer chains to reduce self quenching. All the PBS suspensions of PSFF coated silica nanoparticles show stable optical properties. After 3 weeks storage in the dark, no measurable decrease of fluorescence occurred.

TABLE 4

Optical Properties and Stern-Volmer Constants of NPs

| Entry | $\lambda_{abs}$/nm | $\epsilon_{max}$/ L mol$^{-1}$ cm$^{-1a}$ | $\lambda_{flu}$/nm | $K_{SV}$/ppm | $\Phi_{flu}$ (%) |
|---|---|---|---|---|---|
| PSFF in toluene | 341 | 18000 | 385 | 0.0028[b] | 22 |
| PSFF coated NPs | 336 | 15000 | 443 | 0.025[b] | 4 |
| PSFF coated $C_{18}$ modified NPs | 340 | 23700 | 442 | 0.10[b] | 10 |
| Silane-PSFF coated NPs | 336 | 46100 | 443 | 0.11[b], 0.047[c] | 13 |

[a]Absorptivities are calculated per mole of silicon.
[b]TNT detection. $K_{sv}$ is calculated from the emission intensity at 443 nm except $K_{sv}$ of PSFF in toluene which is calculated from emission intensity at 385 nm.
[c]RDX detection. $K_{sv}$ is calculated from the emission intensity at 443 nm.

TNT and RDX detection was quantified by adding a small aliquot of an acetone solution of TNT or an acetonitrile solution of RDX into a pH 7.4 PBS suspension of nanoparticles while monitoring the fluorescence quenching. The concentrations of nanoparticles were 0.1 mg mL$^{-1}$ silica particles in PBS for PSFF coated plain spheres and PSFF coated $C_{18}$ modified spheres and 0.02 mg mL$^{-1}$ silica particles in PBS for silane-PSFF coated spheres. The quenching response was analyzed by fitting the data to the Stern-Volmer equation.

FIGS. 8A & 8B respectfully show the decrease observed in fluorescence intensity of silane-PSFF coated silica nanoparticles with the addition of dissolved TNT and RDX at low concentrations. In FIGS. 8A and 8B, the quenching of PSFF fluorescence varied with the analyte used. The curves represent different concentrations of analyte, with a baseline having no analyte. For TNT each increment was 0.2 ppm TNT and for RDX each increment. Emission quenching by TNT led to a greater decrease at the low energy wavelength side of the emission band. However, emission quenching with RDX showed a greater decrease on the high energy side of the emission band. This suggests that the explosive analytes may be coadsorbed on the silica in close proximity to the polymer so that a better energy match between the fluorophore and the LUMO (lowest unoccupied molecular orbital) of RDX or TNT enhances quenching for RDX on the high energy side of the emission and for TNT toward the low energy. The LUMO of TNT is known to be significantly below that of RDX.

The conservative detection limits in the results are believed to be the first significant observable fluorescence quenching caused by the addition of the explosive. This can be seen in FIG. 8A for addition of a 200 ppb aliquot of TNT into silane-PSFF coated NPs suspension. Since the concentrations of silica nanoparticles in PBS buffer are 0.1 mg mL$^{-1}$ and 0.02 mg mL$^{-1}$, respectively, the effective concentrations of the active fluorophore PSFF on those two kinds of NPs are only 1.8 mg mL$^{-1}$ and 0.7 mg mL$^{-1}$, respectively. Stern-constants in Table 2 show the PSFF coated silica nanoparticles to be 35 times more sensitive for aqueous TNT when compared with TNT detection in toluene by soluble PSFF. A lower sensitivity was obtained with PSFF adsorbed plain nanoparticles, since the detection limit of TNT was 1 ppm even though the concentration of PSFF in suspension is 5.1 mg mL$^{-1}$. In this case, the high density of PSFF on the surface of silica nanoparticles not only increases the formation of excimer and decreases the quantum yield, as noted above, but it also may hinder access of the TNT molecules to the polymer chains. The detection limit of RDX by silane-PSFF coated spheres is 800 ppb. To the knowledge of the present inventors at the time of the invention, this is the first example of the detection of aqueous RDX by fluorescence quenching with a luminescent polymer. Compared with other methods of detecting aqueous explosives, such as square-wave voltammetry sensing whose detection limit is as low as 20 ppb for TNT in seawater and 120 ppb for RDX in soil samples, fluorescence quenching of PSFF coated silica nanoparticles is simple and has the potential to be a field test for aqueous explosives. The sensitivity obtained by supporting the fluorophore on an adsorptive silica nanoparticle exceeds that of cyclodextrin encapsulated fluorophores (as detailed in US EPA Method 8330).

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A sensor for high explosives, comprising a thin layer of fluorescent polymer covalently linked to a support with an oxide surface, wherein said fluorescent polymer comprises a copolymer of one of the group consisting of silafluorene, silole, spirofluorene and fluorene and their derivatives, and a capping moiety of a trimethoxysilyl cap/end group that covalently attaches said fluorescent polymer to surface hydroxides of said oxide surface.

2. The sensor of claim 1, wherein said support comprises a silica support.

3. The sensor of claim 1, wherein said silica support comprises a silica chromatographic support.

4. The sensor of claim 3, wherein said fluorescent polymer comprises one or a few monolayers on said silica chromatographic support.

5. The sensor of claim 3, wherein said chromatographic support comprises a silica gel thin layer chromatographic plate.

6. The sensor of claim 1 wherein said support comprises a porous nanostructure.

7. The sensor of claim 6, wherein said porous nanostructure comprises a silica nanoparticle.

8. The sensor of claim 1, wherein said fluorescent polymer comprises poly(silafluorenyldiethynylspirobifluorene).

9. The sensor of claim 8, wherein said capping moiety comprises one of $SiMe_2Ph$ and $Si(OCH_3)_3$.

10. The sensor of claim 1, wherein said fluorescent polymer comprises poly(silafluorenyldiethynylfluorenyl).

11. The sensor of claim 10, wherein said capping moiety comprises one of $SiMe_2Ph$ and $Si(OCH_3)_3$.

12. The sensor of claim 1, wherein said fluorescent polymer comprises poly(silolediethynylspirobifluorene).

13. The sensor of claim 12, wherein said capping moiety comprises one of $SiMe_2Ph$ and $Si(OCH_3)_3$.

14. A method for forming a sensor for high explosives, the method comprising preparing a fluorescent polymer that is a copolymer of one of the group consisting of silafluorene, silole, spirofluorene and fluorene, capping the reactive polymer via hydrosilation with trimethoxysilane, and reacting the trimethoxysilane with surface hydroxides of a support to covalently bond the fluorescent polymer with the surface hydroxides.

15. A sensor for high explosives, comprising poly(silolediethynylspirobifluorene) covalently attached to a porous nanostructure within or upon the porous nanostructure.

16. The sensor of claim 15, wherein said porous nanostructure comprises a silica nanoparticle.

17. The sensor of claim 15, wherein said porous nanostructure comprises a nanoparticle of octadecyl modified silica.

18. The sensor of claim 1, wherein said thin layer of fluorescent polymer consists of one or a few monolayers.

19. The sensor of claim 1, wherein said support with an oxide surface comprises a chromatographic support.

* * * * *

UNITED STATES PATENT AND TRADEMARK OFFICE
CERTIFICATE OF CORRECTION

PATENT NO.         : 9,134,239 B2                                    Page 1 of 1
APPLICATION NO.    : 13/426149
DATED              : September 15, 2015
INVENTOR(S)        : William C. Trogler et al.

It is certified that error appears in the above-identified patent and that said Letters Patent is hereby corrected as shown below:

In the Specification:

| | |
|---|---|
| Col. 4, line 29 | Please delete "of class" and insert --class of-- therefor. |
| Col. 5, line 25 | After "Capping can", please insert --be--. |
| Col. 5, line 39 | Before "sensor", please delete the word "to". |
| Col. 5, line 60 | After "is used", please insert --as--. |
| Col. 6, line 5 | Before "portable", please insert --a--. |
| Col. 10, line 53 | After "DNT", please insert a --,--. |
| Col. 10, line 59 | After "explosives", please insert a --.--. |
| Col. 12, line 6 | After "was", please insert --the--. |
| Col. 12, line 61 | Please delete "posses" and insert --possess-- therefor. |
| Col. 14, line 54 | Please delete "Stern-constants" and insert --Stern-Volmer constants-- therefor. |

Signed and Sealed this
Fourteenth Day of June, 2016

Michelle K. Lee
*Director of the United States Patent and Trademark Office*